(12) United States Patent
Mitchell et al.

(10) Patent No.: US 8,027,035 B2
(45) Date of Patent: *Sep. 27, 2011

(54) NON-ORTHOGONAL PARTICLE DETECTION SYSTEMS AND METHODS

(75) Inventors: John Mitchell, Longmont, CO (US); Jon Sandberg, Erie, CO (US); Karen R. Sandberg, Legal Representative, Shelton, WA (US); Dwight A. Sehler, Longmont, CO (US)

(73) Assignee: Particle Measuring Systems, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/043,305

(22) Filed: Mar. 8, 2011

(65) Prior Publication Data
US 2011/0155927 A1    Jun. 30, 2011

Related U.S. Application Data

(63) Continuation of application No. 12/326,335, filed on Dec. 2, 2008, now Pat. No. 7,916,293.

(60) Provisional application No. 61/107,397, filed on Oct. 22, 2008, provisional application No. 61/005,336, filed on Dec. 4, 2007, provisional application No. 60/992,192, filed on Dec. 4, 2007.

(51) Int. Cl.
*G01N 15/02* (2006.01)

(52) U.S. Cl. ...................................... 356/336

(58) Field of Classification Search .......... 356/335–338, 356/340, 342
See application file for complete search history.

(56) References Cited

U.S. PATENT DOCUMENTS

| | | | |
|---|---|---|---|
| 2,643,541 A | 6/1953 | McCreary |
| 3,200,373 A | 8/1965 | Rabinow |
| 3,303,466 A | 2/1967 | Holt |
| 3,406,289 A | 10/1968 | Schleusener |
| 3,422,422 A | 1/1969 | Frank et al. |
| 3,534,289 A | 10/1970 | Clark et al. |
| 3,621,150 A | 11/1971 | Pappas |
| 3,634,823 A | 1/1972 | Dietrich et al. |
| 3,644,743 A | 2/1972 | Binek et al. |
| 3,669,542 A | 6/1972 | Capellaro |
| 3,700,333 A | 10/1972 | Charlson et al. |
| 3,705,771 A | 12/1972 | Friedman et al. |
| 3,718,868 A | 2/1973 | Pao et al. |
| 3,753,145 A | 8/1973 | Chesler |

(Continued)

FOREIGN PATENT DOCUMENTS

DE    3338351    5/1984

(Continued)

OTHER PUBLICATIONS

Aikens (Nov. 1990) "Watch Out Photography, Here Come Cooled HCCD Cameras," *Photonics Spectra* 24:95-106.

(Continued)

*Primary Examiner* — Roy M Punnoose
(74) *Attorney, Agent, or Firm* — Greenlee Sullivan P.C.

(57) ABSTRACT

Described herein is a particle detection system capable of spatially resolving the interaction of particles with a beam of electromagnetic radiation. Using a specific electromagnetic beam cross sectional shape and orientation, the detection sensitivity of a particle detection system can be improved. Also provided are methods for detecting and sizing particles in a manner that has low background signal and allows for spatially resolving the scattering or emission of electromagnetic radiation from particles.

21 Claims, 14 Drawing Sheets

U.S. PATENT DOCUMENTS

| | | | |
|---|---|---|---|
| 3,758,787 A | 9/1973 | Sigrist | |
| 3,766,489 A | 10/1973 | Rosenberg et al. | |
| 3,770,351 A | 11/1973 | Wyatt | |
| 3,797,937 A | 3/1974 | Shofner | |
| 3,822,095 A | 7/1974 | Hirschfeld | |
| 3,825,345 A | 7/1974 | Lorenz | |
| 3,835,294 A | 9/1974 | Krohn et al. | |
| 3,851,169 A | 11/1974 | Faxvog | |
| 3,893,766 A | 7/1975 | Hogg | |
| 3,899,748 A | 8/1975 | Bodlaj | |
| 3,941,982 A | 3/1976 | Knollenberg et al. | |
| 3,960,449 A | 6/1976 | Carleton et al. | |
| 3,983,743 A | 10/1976 | Olin et al. | |
| 4,074,939 A | 2/1978 | Rabl | |
| 4,075,462 A | 2/1978 | Rowe | |
| 4,110,043 A | 8/1978 | Eisert | |
| 4,113,386 A | 9/1978 | Lepper | |
| 4,173,415 A | 11/1979 | Wyatt | |
| 4,178,103 A | 12/1979 | Wallace | |
| 4,188,122 A | 2/1980 | Massie et al. | |
| 4,243,318 A | 1/1981 | Stöhr | |
| 4,272,193 A | 6/1981 | Eastman et al. | |
| 4,273,443 A | 6/1981 | Hogg | |
| 4,274,745 A | 6/1981 | Takahashi et al. | |
| 4,281,924 A | 8/1981 | Aver et al. | |
| 4,284,355 A | 8/1981 | Hansen et al. | |
| 4,291,983 A | 9/1981 | Kraft et al. | |
| 4,318,180 A | 3/1982 | Lundquist et al. | |
| 4,329,054 A | 5/1982 | Bachalo | |
| 4,338,024 A | 7/1982 | Bolz et al. | |
| 4,348,111 A | 9/1982 | Goulas et al. | |
| 4,361,400 A | 11/1982 | Gray et al. | |
| 4,387,993 A | 6/1983 | Adrian | |
| 4,411,525 A | 10/1983 | Ogawa | |
| 4,429,995 A | 2/1984 | Goulas | |
| 4,444,500 A | 4/1984 | Flinsberg et al. | |
| 4,496,839 A | 1/1985 | Bernstein et al. | |
| 4,498,766 A | 2/1985 | Unterleitner | |
| 4,522,494 A | 6/1985 | Bonner | |
| 4,571,079 A | 2/1986 | Knollenberg | |
| 4,573,796 A | 3/1986 | Martin et al. | |
| 4,594,715 A | 6/1986 | Knollenberg | |
| 4,596,464 A | 6/1986 | Hoffman et al. | |
| 4,600,302 A | 7/1986 | Sage, Jr. | |
| 4,609,286 A | 9/1986 | Sage, Jr. | |
| 4,616,927 A | 10/1986 | Phillips et al. | |
| 4,636,075 A | 1/1987 | Knollenberg | |
| 4,653,056 A | 3/1987 | Baer et al. | |
| 4,661,913 A | 4/1987 | Wu et al. | |
| 4,662,742 A | 5/1987 | Chupp | |
| 4,665,529 A | 5/1987 | Baer et al. | |
| 4,673,820 A | 6/1987 | Kamen | |
| 4,685,802 A | 8/1987 | Saito et al. | |
| 4,693,602 A | 9/1987 | Wyatt et al. | |
| 4,710,642 A | 12/1987 | McNeil | |
| 4,723,257 A | 2/1988 | Baer et al. | |
| 4,728,190 A | 3/1988 | Knollenberg | |
| 4,737,025 A | 4/1988 | Steen | |
| 4,739,177 A | 4/1988 | Borden | |
| 4,739,507 A | 4/1988 | Byer et al. | |
| 4,746,215 A | 5/1988 | Gross | |
| 4,752,131 A | 6/1988 | Eisenlauer et al. | |
| 4,753,530 A | 6/1988 | Knight et al. | |
| 4,764,013 A | 8/1988 | Johnston | |
| 4,781,459 A | 11/1988 | Suzuki | |
| 4,786,165 A | 11/1988 | Yamamoto et al. | |
| 4,798,465 A | 1/1989 | Knollenberg | |
| 4,809,291 A | 2/1989 | Byer et al. | |
| 4,814,868 A | 3/1989 | James | |
| 4,830,494 A | 5/1989 | Ishikawa et al. | |
| 4,850,707 A | 7/1989 | Bowen et al. | |
| 4,872,177 A | 10/1989 | Baer et al. | |
| 4,876,458 A | 10/1989 | Takeda et al. | |
| 4,885,473 A | 12/1989 | Shofner et al. | |
| 4,893,928 A | 1/1990 | Knollenberg | |
| 4,896,048 A | 1/1990 | Borden | |
| 4,917,496 A | 4/1990 | Sommer | |
| 4,920,275 A | 4/1990 | Itoh | |
| RE33,213 E | 5/1990 | Borden | |
| 4,957,363 A | 9/1990 | Takeda et al. | |
| 4,992,190 A | 2/1991 | Shtarkman | |
| 5,033,851 A | 7/1991 | Sommer | |
| 5,033,852 A | 7/1991 | Zaglio | |
| 5,067,814 A | 11/1991 | Suzuki et al. | |
| 5,075,552 A | 12/1991 | McClelland et al. | |
| 5,085,500 A | 2/1992 | Blesner | |
| 5,090,808 A | 2/1992 | Ishikawa et al. | |
| 5,092,675 A | 3/1992 | Sommer | |
| 5,101,113 A | 3/1992 | Hirleman, Jr. et al. | |
| 5,121,988 A | 6/1992 | Blesner et al. | |
| 5,153,926 A | 10/1992 | Jansson et al. | |
| 5,156,461 A | 10/1992 | Moslehi et al. | |
| 5,159,397 A | 10/1992 | Kosaka et al. | |
| 5,159,398 A | 10/1992 | Maekawa et al. | |
| 5,262,841 A | 11/1993 | Blesner et al. | |
| 5,282,151 A * | 1/1994 | Knollenberg | 702/26 |
| 5,285,467 A | 2/1994 | Scheps | |
| 5,329,351 A | 7/1994 | Clementi | |
| RE34,729 E | 9/1994 | Sipes, Jr. | |
| 5,370,842 A | 12/1994 | Miyazaki et al. | |
| 5,396,333 A | 3/1995 | Aleshin et al. | |
| 5,402,438 A | 3/1995 | Tanuma | |
| 5,412,466 A | 5/1995 | Ogino | |
| 5,428,451 A | 6/1995 | Lea et al. | |
| 5,459,569 A | 10/1995 | Knollenberg et al. | |
| 5,467,188 A | 11/1995 | Miyashita | |
| 5,467,189 A | 11/1995 | Kreikebaum et al. | |
| 5,471,515 A | 11/1995 | Fossum et al. | |
| 5,475,487 A | 12/1995 | Mariella et al. | |
| 5,481,357 A | 1/1996 | Ahsan et al. | |
| 5,515,164 A | 5/1996 | Kreikebaum et al. | |
| 5,565,984 A | 10/1996 | Girvin | |
| 5,576,827 A * | 11/1996 | Strickland et al. | 356/336 |
| 5,594,544 A | 1/1997 | Horiuchi et al. | |
| 5,600,438 A | 2/1997 | Kreikebaum | |
| 5,642,193 A | 6/1997 | Girvin et al. | |
| 5,654,797 A | 8/1997 | Moreau et al. | |
| 5,671,046 A | 9/1997 | Knowlton | |
| 5,726,753 A | 3/1998 | Sandberg | |
| 5,751,422 A | 5/1998 | Mitchell | |
| 5,805,281 A | 9/1998 | Knowlton et al. | |
| 5,825,487 A | 10/1998 | Felbinger et al. | |
| 5,841,126 A | 11/1998 | Fossum et al. | |
| 5,861,950 A | 1/1999 | Knowlton | |
| 5,864,399 A | 1/1999 | Girvin et al. | |
| 5,870,190 A | 2/1999 | Unger | |
| 5,872,361 A | 2/1999 | Paoli et al. | |
| 5,887,439 A | 3/1999 | Kotliar | |
| 5,889,589 A | 3/1999 | Sandberg | |
| 5,920,388 A | 7/1999 | Sandberg et al. | |
| 5,946,092 A | 8/1999 | DeFreez et al. | |
| 5,946,093 A | 8/1999 | DeFreeze et al. | |
| 6,003,389 A | 12/1999 | Flagan et al. | |
| 6,005,619 A | 12/1999 | Fossum | |
| 6,016,194 A | 1/2000 | Girvin et al. | |
| 6,067,157 A | 5/2000 | Altendorf | |
| 6,091,494 A | 7/2000 | Kreikebaum | |
| 6,104,491 A | 8/2000 | Trainer | |
| 6,137,572 A | 10/2000 | DeFreeze et al. | |
| 6,167,107 A | 12/2000 | Bates | |
| 6,181,419 B1 | 1/2001 | Snelling et al. | |
| 6,211,956 B1 | 4/2001 | Nicoli | |
| 6,249,341 B1 | 6/2001 | Basiji et al. | |
| 6,256,096 B1 | 7/2001 | Johnson | |
| 6,275,288 B1 | 8/2001 | Atkinson et al. | |
| 6,323,949 B1 * | 11/2001 | Lading et al. | 356/477 |
| 6,404,494 B1 | 6/2002 | Masonis et al. | |
| 6,414,754 B1 | 7/2002 | Johnson | |
| 6,465,802 B1 | 10/2002 | Matsuda | |
| 6,628,386 B2 | 9/2003 | Davies et al. | |
| 6,680,800 B1 | 1/2004 | Schreiber et al. | |
| 6,710,878 B1 | 3/2004 | Dean et al. | |
| 6,768,545 B2 | 7/2004 | Matsuda et al. | |
| 6,784,981 B1 | 8/2004 | Roche et al. | |
| 6,813,303 B2 | 11/2004 | Matsuda et al. | |
| 6,859,277 B2 | 2/2005 | Wagner et al. | |
| 6,903,818 B2 | 6/2005 | Cerni et al. | |

| | | | |
|---|---|---|---|
| 6,906,792 B2 | 6/2005 | Ortyn et al. | |
| 6,919,960 B2 | 7/2005 | Hansen et al. | |
| 7,030,980 B1 | 4/2006 | Sehler et al. | |
| 7,053,783 B2 | 5/2006 | Hamburger et al. | |
| 7,075,647 B2 | 7/2006 | Christodoulou | |
| 7,113,266 B1* | 9/2006 | Wells | 356/73 |
| 7,162,057 B1 | 1/2007 | Roth et al. | |
| 7,170,601 B2 | 1/2007 | Matsuda | |
| 7,221,453 B2 | 5/2007 | Sharpe et al. | |
| 7,221,457 B2 | 5/2007 | Jorgenson et al. | |
| 7,258,774 B2 | 8/2007 | Chou et al. | |
| 7,456,960 B2 | 11/2008 | Cerni et al. | |
| 7,518,723 B2* | 4/2009 | Adams et al. | 356/338 |
| 7,576,857 B2 | 8/2009 | Wagner | |
| 7,916,293 B2* | 3/2011 | Mitchell et al. | 356/336 |
| 2002/0057432 A1 | 5/2002 | Ortyn et al. | |
| 2003/0020910 A1 | 1/2003 | Peterson et al. | |
| 2004/0042008 A1 | 3/2004 | Wagner et al. | |
| 2004/0067167 A1 | 4/2004 | Zhang et al. | |
| 2004/0080747 A1 | 4/2004 | Cerni et al. | |
| 2005/0030519 A1 | 2/2005 | Roth | |
| 2005/0136548 A1 | 6/2005 | McDevitt et al. | |
| 2006/0001874 A1 | 1/2006 | Matsuda | |
| 2006/0038998 A1 | 2/2006 | Wagner | |
| 2006/0221325 A1* | 10/2006 | Wells | 356/73 |
| 2006/0244965 A1 | 11/2006 | Ichijo | |
| 2006/0274309 A1 | 12/2006 | Cerni et al. | |
| 2007/0146703 A1 | 6/2007 | Adams et al. | |
| 2007/0146873 A1* | 6/2007 | Ortyn et al. | 359/386 |
| 2007/0165225 A1 | 7/2007 | Trainer | |
| 2009/0073649 A1 | 6/2009 | Mitchell et al. | |
| 2009/0190128 A1 | 7/2009 | Cerni | |
| 2009/0219530 A1 | 9/2009 | Mitchell et al. | |
| 2009/0244536 A1 | 10/2009 | Mitchell et al. | |
| 2009/0268202 A1 | 10/2009 | Wagner | |
| 2010/0225913 A1* | 9/2010 | Trainer | 356/338 |

FOREIGN PATENT DOCUMENTS

| | | |
|---|---|---|
| EP | 0 015 170 | 9/1980 |
| EP | 0300875 | 1/1989 |
| EP | 0 463 562 | 1/1992 |
| EP | 0 562 630 | 9/1993 |
| EP | 0 504 185 | 3/1994 |
| GB | 1497698 | 1/1978 |
| JP | 60-209147 | 10/1985 |
| JP | 63-11838 | 1/1988 |
| JP | 4-184241 | 7/1992 |
| JP | 4-289440 | 10/1992 |
| JP | 4-369464 | 12/1992 |
| JP | 9-113436 | 5/1997 |
| JP | 9-311103 | 12/1997 |
| JP | 10-2856 | 1/1998 |
| JP | 11-197868 | 7/1999 |
| JP | 11211650 | 8/1999 |
| JP | 2000-22265 | 1/2000 |
| JP | 2000-512390 | 9/2000 |
| JP | 2002-223019 | 8/2002 |
| JP | 3480669 | 12/2003 |
| WO | WO 90/10216 | 9/1990 |
| WO | WO 92/08120 | 5/1992 |
| WO | WO 99/02966 | 1/1999 |
| WO | WO 01/27686 | 4/2001 |
| WO | WO 02/29106 | 4/2002 |
| WO | WO 2004/031742 | 4/2004 |
| WO | WO 2005/095925 | 10/2005 |
| WO | WO 2005/100954 | 10/2005 |
| WO | WO 2006/067977 | 6/2006 |
| WO | WO 2006/132980 | 12/2006 |
| WO | WO 2007/029480 | 3/2007 |
| WO | WO 2009/073649 | 6/2009 |
| WO | WO 2009/073652 | 6/2009 |

OTHER PUBLICATIONS

Altmann et al. (Mar. 15, 1981) "Two-Mirror Multipass Absorption Cell," *Applied Optics* 20(6):995-999.

Amnis (2004) "Time Delay Integration: Enabling High Sensitivity Detection for Imaging-in-Flow on the Image Stream® 100 Cell Analysis System," http://dp.univr.it/~laudanna/Systems%20Biology/Technologies/ImageStream/Tech%20Notes/Technology%20Report%20Time%20Delay%20Integration.pdf.

Arashiki, S. (Oct. 1999) "Detection Principle and Performance of the Liquid-Borne Particle Counters," *RION Technical Notes* 616-2: 6 pages.

Borso, C.S. (1982) "Optimization of Monolithic Solid State Array Detectors for the Positionin Encoding of Small Angle X-Ray Scattering from Synchrotron Sources," *Nuc. Instrom. Meth.* 204:65-72.

British Search Report, Corresponding to Great British Application No. GB 0318240.9, Completed Dec. 15, 2003.

Cerni, T.A. (2001) "High Sensitivity, High Sample Rate, Aerosol Optical Particle Counter," *Clean Technol.* 11(6):12-14.

Dalsa (2005) "CCD VS. CMOS," http://www.dalsa.com/corp/markets/CCD_vs_CMOS.aspx.

Faxvog (Oct. 1976) "New Laser Particle Sizing Instrument," Research Publication GMR-2263, Research Laboratories, General Motors Corporation, Warren Michigan.

Herriott et al. (Apr. 1964) "Off-Axis Paths in Spherical Mirror Interferometers," *Applied Optics* 3(4):523-526.

Herriott et al. (Aug. 1965) "Folded Optical Delay Lines," *Applied Optics* 4(8):883-889.

International Search Report and Written Opinion Corresponding to International Application No. PCT/US2008/085243, Mailed Jan. 30, 2009.

International Search Report and Written Opinion Corresponding to International Application No. PCT/US2006/021483, Mailed Feb. 11, 2006.

International Search Report and Written Opinion, Corresponding to International Application No. PCT/US2008/085236, Mailed Feb. 5, 2009.

Japanese Official Action, Corresponding to Japanese Application No. 2003-303709, Mailed Mar. 31, 2009.

Japanese Official Action, Corresponding to Japanese Application No. 2003-303709, Mailed Feb. 2, 2010.

Knollenberg et al. (1991) "Optical Particle Monitors, Counters and Spectrometers: Performance, Characterization, Comparison and Use," *Proceedings of the Institute of Environmental Sciences Conference*, San Diego, California, pp. 751-771.

Knollenberg et al. (Jan. 1987) "In Situ Optical Particle Size Measurements in Liquid Media," Proceedings of Pure Water Conference, Palo Alto California, Jan. 13-14.

Knollenberg, R.G. (1987) "Sizing Particles at High Sensitivity in High Molecular Scattering Environments," *Proc Int. Environ. Sci.*

Knollenberg, R.G. (1992) "The Design of a High Sensitivity Large Sample Volume Particle Counter for Ultra Clean DI Water," *Microcontamination 92 Conference Proceedings*, Santa Clara, CA, pp. 764-776.

Knollenberg, R.G. (Jan./Feb. 1985) "The Measurement of Particle Sizes below 0.1 Micrometers," *J. Environ. Sci.* :32-51.

Knowlton, D.K. (1998) "Inviscid Jet Technology for Monitoring Particles in Fluids," *Proceedings 1998 Institute of Environmental Sciences and Technology* pp. 34-39.

Liu et al. (Apr. 2000) "CMOS Uncooled Heat-Balancing Infrared Imager," *IEEE J. Solid-State Circuits* :1-9.

Micron (Jan. 2004) "1.3-Megapixel CMOS Active-Pixel Digital Image Sensor," Micron Document No. Mt0M43C365TC.fm—Ver. 3.0, http://www.micron.com/products/imaging/products/MT9M413.html.

Rion "Liquid-Borne Particle Counter for Pure Water Model XP-L4," Technical Information, Tokyo Japan, Non Dated.

Rion "Particle Counter KS-41 for photoresist measurement" www.mgintl.com/pdf/LPC_for_Resist_e.ppt Unknown Publication Date.

Schuster et al. (Jul. 1972) "Detection and Sizing of Small Particles in an Open Cavity Gas Laser," *Appl. Opt.* 11(7):1515-1520.

Tezcan et al. (Feb. 2003) "A Low-Cost Uncooled Infrared Microbolometer Detector in Standard CMOS Technology," *IEEE Trans. Electron Dev.* 50(2):494-502.

Titus, H. (Feb. 2001) "Imaging Sensors that Capture your Attention," *Sensors* 18(2).

Ueki et al. (Dec. 25, 1992) "Flow Velocimeter with Wide-Stripe Semiconductor Laser," *Collection of Papers of the Japan Society of Mechanical Engineers* 58(556):171-175.

Ueki et al. (Jul. 1992) "Semiconductor Laser 2-Focus Velocimeter and the Application Thereof," *The 29$^{th}$ Lecture Meeting of Turbomachinery Society in Toyama, Japan, Turbomachinery Society*, pp. 241-244.

von Freyhold et al. (Nov. 2002) "Powerful Laser Diodes Become High-Brightness Laser Tools," *Photonics Showcase* pp. 5-6.

* cited by examiner

NON-ORTHOGONAL PARTICLE DETECTION SYSTEMS AND METHODS

CROSS REFERENCE TO RELATED APPLICATION

This application is a continuation of U.S. patent application Ser. No. 12/326,335, filed on Dec. 2, 2008 now U.S. Pat. No. 7,916,293, which claims priority under 35 U.S.C. §119 (e) to U.S. Provisional Patent Application Nos. 61/005,336, 60/992,192 and 61/107,397 filed on Dec. 4, 2007, Dec. 4, 2007, and Oct. 22, 2008, respectively, all of which are hereby incorporated by reference in their entireties.

STATEMENT REGARDING FEDERALLY SPONSORED RESEARCH OR DEVELOPMENT

Not Applicable.

BACKGROUND OF THE INVENTION

This invention is in the field of optical particle counters. This invention relates generally to an optical particle counter capable of spatially resolving electromagnetic radiation scattered off of or emitted by particles. This invention also relates to methods for detecting and sizing particles and methods for spatially resolving an interaction of particles with a beam of electromagnetic radiation A large portion of the micro-contamination industry is reliant on the use of particle counters, such as are described in a large number of U.S. patents, including U.S. Pat. Nos. 3,851,169, 4,348,111, 4,957,363, 5,085,500, 5,121,988, 5,467,188, 5,642,193, 5,864,399, 5,920,388, 5,946,092, and 7,053,783. U.S. Pat. Nos. 4,728,190, 6,859,277, and 7,030,980, 5,282,151 also disclose particle counters and are hereby incorporated by reference in their entirety. Aerosol particle counters are often used to measure air-born particle contamination in clean-rooms and clean zones. Liquid phase particle counters are often used to measure particulate contamination in the water treatment and chemical processing industries.

Particle counters capable of spatially resolving electromagnetic radiation scattered or emitted by particles typically employ two-dimensional detectors, such as the particle detector described in U.S. Pat. No. 5,282,151. U.S. Pat. No. 7,170,601 and U.S. Patent Application Publication No. US 2006/0001874 A1 also disclose a particle counter capable of spatially resolving electromagnetic radiation scattered or emitted by particles. These optical particle counters collect scattered or emitted electromagnetic radiation in a direction parallel to the fluid flow direction and are capable of spatially resolving the source of scattered or emitted electromagnetic radiation along directions perpendicular to the fluid flow direction. These particle counters, however, lack the ability to spatially resolve scattered or emitted electromagnetic radiation in a direction parallel to the fluid flow direction. The particle detection systems described herein utilize a geometrical configuration which allows for spatially resolving electromagnetic radiation scattered or emitted by particles in directions parallel to the fluid flow direction as well as perpendicular to the fluid flow direction.

SUMMARY OF THE INVENTION

Described herein is a particle detection system capable of spatially resolving the interaction of particles with a beam of electromagnetic radiation. Using a specific electromagnetic beam cross sectional shape and orientation, the detection sensitivity of a particle detection system can be improved. Also described herein are methods for detecting and sizing particles in a manner that has low background signal and allows for spatially resolving the scattering or emission of electromagnetic radiation from particles.

In an embodiment, a particle detection system comprises a flow cell for containing a fluid flowing through the flow cell in a flow direction; a source for generating a beam of electromagnetic radiation having a cross sectional profile having a major axis and a minor axis, the source positioned to direct the beam through the flow cell, wherein the angle between the major axis of the cross sectional profile of the beam and the flow direction is non-orthogonal, and wherein particles contained within the fluid interact with the beam thereby generating scattered or emitted electromagnetic radiation; and a two-dimensional detector positioned in optical communication with the flow cell for receiving at least a portion of the scattered or emitted electromagnetic radiation.

Particle detection systems such as these are useful with methods of detecting and/or sizing particles. In an embodiment, a method of this aspect comprises the steps of: providing particles in a fluid having a flow direction; passing a beam of electromagnetic radiation having a cross sectional profile having a major axis and a minor axis through the fluid, wherein the angle between the major axis and the flow direction is non-orthogonal and wherein particles interact with the beam thereby generating scattered or emitted electromagnetic radiation; and detecting at least a portion of the scattered or emitted electromagnetic radiation with a two-dimensional detector, thereby detecting the particles. In an embodiment preferred for some applications, the scattered or emitted electromagnetic radiation is collected or directed onto the two-dimensional detector by a system of optics. In some embodiments, the angle between the beam cross sectional major axis and the flow direction is non-parallel.

Any optical element may be useful with the methods and systems described herein including, but not limited to: a lens, a mirror, a filter, a beam splitter, an optical fiber, an optical waveguide, a window, an aperture, a slit, a prism, a grating, a polarizer, a wave plate, a crystal, and any combination of these or other optical elements. In an embodiment preferred for some applications, the scattered or emitted electromagnetic radiation is imaged onto the two-dimensional detector by the system of optics. For some embodiments, a particle counter optionally includes auto-focusing of the system of optics to properly image scattered or emitted radiation from a particle onto a two-dimensional detector.

In an embodiment preferred for some applications, useful two-dimensional detectors comprise an array of detector elements positioned such that a plurality of detector elements receive the scattered or emitted electromagnetic radiation. Any two-dimensional detector can be useful with the systems and methods for detecting or sizing particles including, but not limited to: a two-dimensional array of photodetectors, a charge-coupled device (CCD) detector, a complementary metal-oxide-semiconductor (CMOS) detector, a metal-oxide-semiconductor (MOS) detector, an active pixel sensor, a microchannel plate detector, a two-dimensional array of photomultiplier tubes, a two-dimensional array of photodiodes, a two-dimensional array of phototransistors, a two-dimensional array of photoresistors, and a photoconductive film.

In embodiments preferred for some applications, the two-dimensional detector has an orientation positioned to allow for a sharply focused image of the scattered or emitted electromagnetic radiation across an active area of the two-dimensional detector. In an embodiment preferred for some applications, the two-dimensional detector has an orientation positioned for providing a spatially resolved image of the scattered or emitted electromagnetic radiation, wherein the scattered or emitted electromagnetic radiation is spatially resolved in a first direction parallel to a propagation axis of the beam and in a second direction parallel to the flow direction. In another embodiment, the orientation of the two-dimensional detector provides for a spatially resolved image of the scattered or emitted electromagnetic radiation in a first direction parallel to a propagation axis of the beam and in a second direction parallel to the major axis of the beam cross sectional profile.

In another aspect, methods are provided for spatially resolving an interaction of particles with a beam of electromagnetic radiation. A method of this aspect comprises the steps of: providing particles suspended within a fluid flowing in a flow direction; passing a beam of electromagnetic radiation through the fluid, wherein the beam has a cross sectional profile having a major axis and a minor axis and wherein the angle between the major axis and the flow direction is non-orthogonal and wherein the particles interact with the beam thereby generating scattered or emitted electromagnetic radiation; and directing at least a portion of the scattered or emitted electromagnetic radiation onto a two-dimensional detector, thereby spatially resolving the scattered or emitted electromagnetic radiation in a first direction parallel to a propagation axis of the beam and in a second direction parallel to the major axis of the beam cross sectional profile. For embodiments, when the scattered or emitted electromagnetic radiation reaches the two-dimensional detector, it is detected by the two-dimensional detector, thereby generating a plurality of output signals corresponding to intensities of the scattered or emitted electromagnetic radiation. In some embodiments, the angle between the beam cross sectional major axis and the flow direction is non-parallel.

In an embodiment preferred for some applications, the electromagnetic radiation scattered or emitted by the particles is spatially resolved from electromagnetic radiation scattered or emitted by walls of a flow cell surrounding the fluid. In another embodiment, electromagnetic radiation scattered or emitted by a first particle interacting with the beam is imaged onto a first position of the two-dimensional detector and scattered or emitted electromagnetic radiation generated by a second particle, having a different position than the first particle, is imaged onto a second position of the two-dimensional detector.

In some embodiments of this aspect, the method further comprises analyzing a signal provided by the detector in response to the scattered or emitted electromagnetic radiation. In an embodiment, the analysis comprises one or more techniques including time delay integration (TDI), image threshold analysis, image shape analysis, pulse height analysis, pulse width analysis, or other techniques useful for detecting particles.

In another aspect, methods are provided for sizing a particle. A method of this aspect comprises the steps of: providing a particle suspended within a fluid flowing in a flow direction through a flow cell; passing a beam of electromagnetic radiation through the fluid, wherein the beam has a cross sectional profile having a major axis and a minor axis and wherein the angle between the major axis and the flow direction is non-orthogonal and wherein the particle interacts with the beam thereby generating scattered or emitted electromagnetic radiation; imaging at least a portion of the scattered or emitted electromagnetic radiation onto a two-dimensional detector; determining the intensity of the scattered or emitted electromagnetic radiation on the two-dimensional detector; and comparing the intensity of the scattered or emitted electromagnetic radiation with one or more threshold reference values, thereby determining the size of the particle. For example, the threshold reference values may correspond to intensities of scattered or emitted electromagnetic radiation from particles of known sizes; if the intensity of electromagnetic radiation scattered or emitted from a particle falls between two threshold reference values, the particle is sized between the known particle sizes corresponding to those threshold reference values.

In an embodiment of this aspect, the threshold reference values are dependent upon the position of the particle within the flow cell. In another embodiment, the threshold reference values are dependent upon the flow rate of the fluid. In yet another embodiment, the flow rate of the fluid may be dependent upon the position within the flow cell; for example, fluid flowing near the walls of the flow cell may be flowing slower than fluid flowing near the center of the flow cell. In another embodiment, the threshold reference values are dependent upon the intensity of the beam. In a further embodiment, the threshold reference values are dependent upon both the intensity of the beam and the position within the flow cell.

In an embodiment preferred for some applications, the method may further comprise the step of determining the position of the particle within the flow cell. In some embodiments, this step is preferred to occur before the step of comparing the intensity of the scattered or emitted electromagnetic radiation with one or more threshold reference values. In another embodiment, the position of the particle within the flow cell is used to determine one or more threshold reference values for subsequent comparison.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

DETAILED DESCRIPTION OF THE INVENTION

Figure 1:
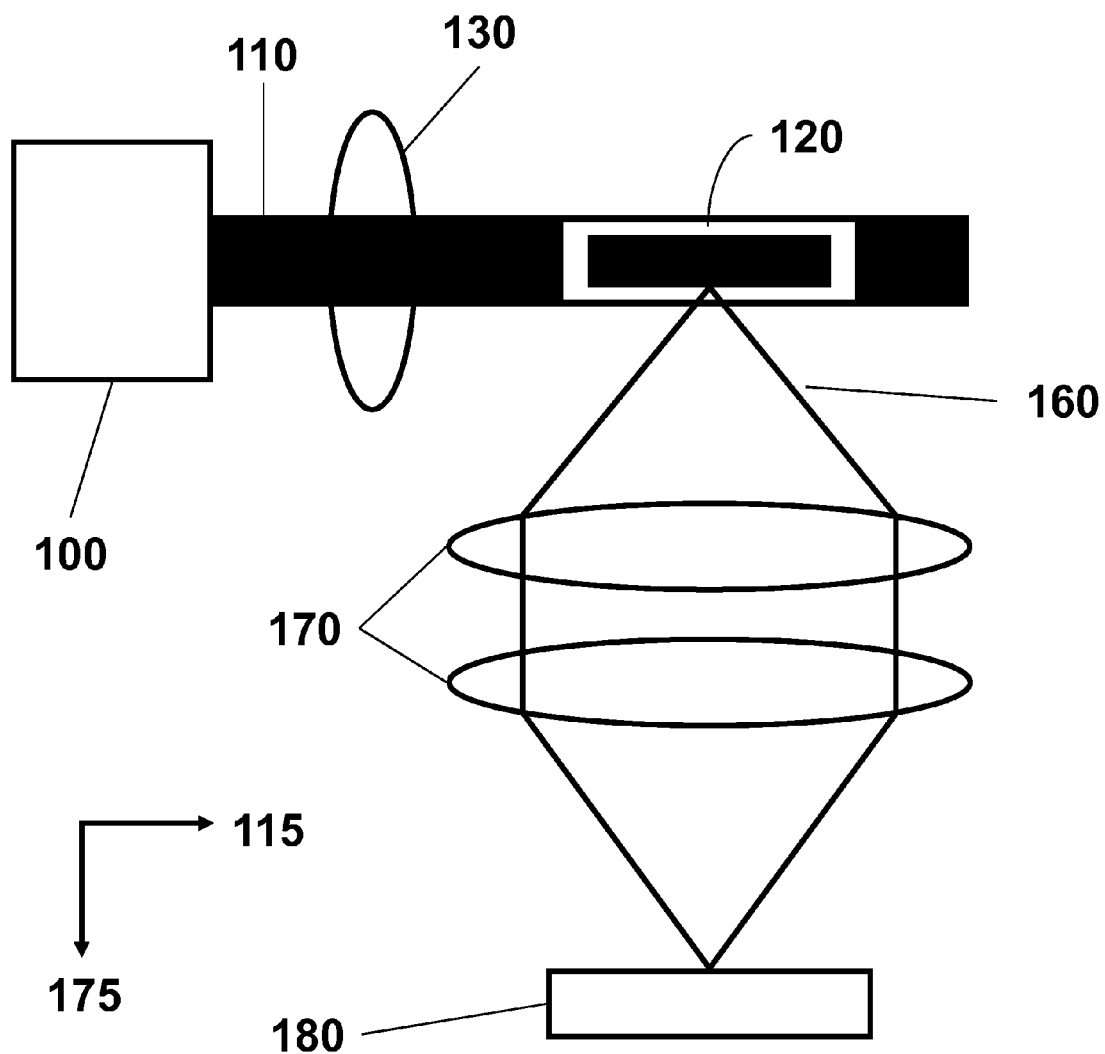
FIG. 1 provides a schematic diagram of an embodiment of a particle detection system.

In general the terms and phrases used herein have their art-recognized meaning, which can be found by reference to standard texts, journal references and contexts known to those skilled in the art. The following definitions are provided to clarify their specific use in the context of the invention.

"Flow direction" refers to an axis parallel to the direction the bulk of a fluid is moving when a fluid is flowing. For fluid flowing through a straight flow cell, the flow direction is parallel to the path the bulk of the fluid takes. For fluid flowing through a curved flow cell, the flow direction may be considered tangential to the path the bulk of the fluid takes.

"Beam propagation axis" refers to an axis parallel to the direction of travel of a beam of electromagnetic radiation.

"Cross sectional profile" refers to a profile formed by a plane cutting through an object at a right angle to an axis of propagation or travel. For example the cross sectional profile of a beam of electromagnetic radiation is a profile of the beam formed by a plane perpendicular to the beam propagation axis. The cross sectional profile of a flow cell is a profile of the flow cell formed by a plane perpendicular to the flow direction.

"Major axis" refers to an axis parallel to the longest axis of a shape. For example, the major axis of an ellipse is parallel to the longest diameter of the ellipse, and the major axis of a rectangle is parallel to the long dimension of a rectangle.

"Minor axis" refers to an axis parallel to the shortest axis of a shape. For example, the minor axis of an ellipse is parallel to the shortest diameter of the ellipse, and the minor axis of a rectangle is parallel to the short dimension of a rectangle.

"Optical communication" refers to an orientation of components such that the components are arranged in a manner that allows light or electromagnetic radiation to transfer between the components.

"Optical axis" refers to a direction along which electromagnetic radiation propagates through a system.

"Spot size" refers to the size that an image of a point or object is focused to by one or more lenses. In general, the spot size refers to the root mean square (RMS) spot size. The RMS spot size is the size of a spot which includes 66% of the total energy, for example 66% of the total energy of a focused beam of electromagnetic radiation.

"Two-dimensional detector" refers to a detector capable of spatially resolving input signals (e.g., electromagnetic radiation) in two dimensions across an active area of the detector. A two-dimensional detector is capable of generating an image, for example an image corresponding to an intensity pattern on the active area of the detector. A preferred two-dimensional detector comprises an array of detector elements or pixels, for example: a two-dimensional array of photodetectors, a charge-coupled device (CCD) detector, a complementary metal-oxide-semiconductor (CMOS) detector, a metal-oxide-semiconductor (MOS) detector, an active pixel sensor, a microchannel plate detector, a two-dimensional array of photomultiplier tubes, a two-dimensional array of photodiodes, a two-dimensional array of phototransistors, a two-dimensional array of photoresistors, or a photoconductive film.

"Particle" refers to a small object which is often regarded as a contaminant. A particle can be any material created by the act of friction, for example when two surfaces come into mechanical contact and there is mechanical movement. Particles can be composed of aggregates of material, such as dust, dirt, smoke, ash, water, soot, metal, minerals, or any combination of these or other materials or contaminants. "Particles" may also refer to biological particles, for example, viruses, spores and microorganisms including bacteria, fungi, archaea, protists, other single cell microorganisms and specifically those microorganisms having a size on the order of 1-15 µm. A particle may refer to any small object which absorbs or scatters light and is thus detectable by an optical particle counter. As used herein, "particle" is intended to be exclusive of the individual atoms or molecules of a carrier fluid, for example water molecules, oxygen molecules, helium atoms, nitrogen molecules, etc. Some embodiments of the present invention are capable of detecting, sizing, and/or counting particles comprising aggregates of material having a size greater than 50 nm, 100 nm, 1 µm or greater, or 10 µm or greater. Specific particles include particles having a size selected from 50 nm to 50 µm, a size selected from 100 nm to 10 µm, or a size selected from 500 nm to 5 µm.

A particle detection system of some embodiments comprises a flow cell for containing a fluid flowing through the flow cell in a flow direction. In an embodiment preferred for some applications, the flow cell comprises a transparent-walled sample cell. Useful flow cells comprise flow cells capable of transporting fluids comprising liquids or gases. The flow direction of the fluid also provides a reference axis useful for defining additional components of the systems and methods described herein. In an embodiment, the flow cell has a cross sectional profile having a first longer side and a second shorter side. In some embodiments, the first longer side has a length selected from the range of 0.25 mm to 10 mm, preferably 5 mm. In some embodiments, the second shorter side has a width selected from the range of 80 µm to 500 µm, preferably 100 µm. In an embodiment, the flow cell cross section has an aspect ratio, equal to the length of the longer side divided by the width of the shorter side, greater than or equal to 20, or greater than or equal to 50. In some embodiments, the first longer side of the flow cell is aligned parallel to an electromagnetic beam propagation axis and the second shorter side of the flow cell is aligned perpendicular to an electromagnetic beam propagation axis.

A particle detection system of some embodiments also comprises a source for generating a beam of electromagnetic radiation. In a preferred embodiment, the beam of electromagnetic radiation has a cross sectional profile having a major axis and a minor axis. Such a cross sectional profile may be generated by the source itself or by the source in combination with one or more beam shaping elements including lenses, mirrors, apertures, or other beam shaping elements. In some embodiments, the beam cross sectional profile has an elliptical or rectangular shape. In other embodiments, the beam cross sectional profile has a shape that is substantially elliptical or substantially rectangular. In an embodiment preferred for some applications, the beam cross sectional profile has a width along the minor axis selected from between 5 µm and 100 µm, preferably 40 µm. In another embodiment preferred for some applications, the beam cross sectional profile has a width along the major axis selected from between 50 µm and 1200 µm, preferably 600 µm. In an exemplary embodiment, the beam cross sectional profile has a width along the major axis which extends to or beyond the walls of the flow cell. In this and other embodiments, the particle detection system is capable of providing a volumetric analysis of the fluid. In another embodiment, the beam cross sectional profile has a width along the major axis which does not reach the walls of the flow cell. In this and other embodiments, the particle detection system is capable of providing a non-volumetric analysis of the fluid.

In a preferred embodiment, the source is positioned to direct the beam through a flow cell such that the angle between the major axis of the beam cross sectional profile and the flow direction is non-orthogonal. For some embodiments, the angle between the major axis of the beam cross sectional profile and the flow direction is selected from the range of 5° to 85°, or preferably from the range of 16° to 26°, or more preferably from the range of 20° to 22°. In some embodiments, however, the beam cross profile major axis may be orthogonal or parallel to the flow direction.

The particle detection systems in another embodiment further comprise a two dimensional detector positioned in optical communication with the flow cell. A detector positioned in optical communication with the flow cell is useful for detecting at least a portion of electromagnetic radiation that is scattered or emitted by particles interacting with the beam. In an embodiment preferred for some applications, the two-dimensional detector comprises an array of detector elements positioned such that a plurality of detector elements receives at least a portion of the scattered or emitted electromagnetic radiation. Useful two-dimensional detectors include, but are not limited to: a two-dimensional array of photodetectors, a CCD detector, a CMOS detector, a MOS detector, an active pixel sensor, a microchannel plate detector, a two-dimensional array of photomultiplier tubes, a two-dimensional array of photodiodes, a two-dimensional array of phototransistors, a two-dimensional array of photoresistors, and a photoconductive film.

Some embodiments of this aspect may further comprise a system of optics. Optical elements of such a system are useful for shaping the beam of electromagnetic radiation, or for collecting or directing electromagnetic radiation scattered or emitted by particles interacting with the beam onto the two-dimensional detector. A system of optics may comprise one or more optical elements. For example, a system of optics may comprise two aspherical lenses. Useful optical elements include: a lens, a mirror, a filter, a beam splitter, an optical fiber, an optical waveguide, a window, an aperture, a slit, a prism, a grating, a polarizer, a wave plate, a crystal, and any combination of these or other shaping, focusing, or directing elements. In an embodiment preferred for some applications, the system of optics images the scattered or emitted radiation onto the two-dimensional detector. In another embodiment, the scattered or emitted electromagnetic radiation is focused to a spot on the two-dimensional detector having a size selected from the range of 5 µm to 80 µm, preferably 12 µm.

A system of optics for collecting or directing the scattered or emitted electromagnetic radiation is preferably positioned between the flow cell and the two-dimensional detector. In an embodiment, the two-dimensional detector is oriented non-orthogonal to the optical axis of the system of optics for collecting or directing the beam onto the two dimensional detector. Non-orthogonal in this embodiment is in reference to the position of the plane of the two-dimensional detector which contains the active elements in relation to the optical axis of the system of optics.

In another embodiment, the optical axis of the system of optics is oriented non-orthogonal to the major axis of the beam cross sectional profile. In an exemplary embodiment, the two-dimensional detector has an orientation positioned to allow for a sharply focused image of the scattered or emitted electromagnetic radiation across an active area of the two-dimensional detector. In another exemplary embodiment, the two dimensional detector has an orientation positioned for providing a spatially resolved image of the scattered or emitted electromagnetic radiation, wherein the scattered or emitted electromagnetic radiation is spatially resolved along a first axis parallel to the beam propagation axis and along a second axis parallel to the major axis of the beam cross sectional profile.

Referring now to the drawings, FIG. 1 shows a schematic diagram of an embodiment of a particle detection system. As seen in the Figure, source 100 generates a beam of electromagnetic radiation 110 directed through flow cell 120 parallel to beam propagation axis 115. In this embodiment, beam 110 is shaped and directed by a lens 130 before entering flow cell 120. Particles suspended in the fluid flowing through flow cell 120 generate scattered or emitted electromagnetic radiation 160 when they interact with beam 110. An optical system 170 collects and focuses the scattered or emitted electromagnetic radiation 160 along optical detection axis 175 and onto a two-dimensional detector 180. In this embodiment, optical system 170 is comprised of two aspheric lenses.

Figure 2A:
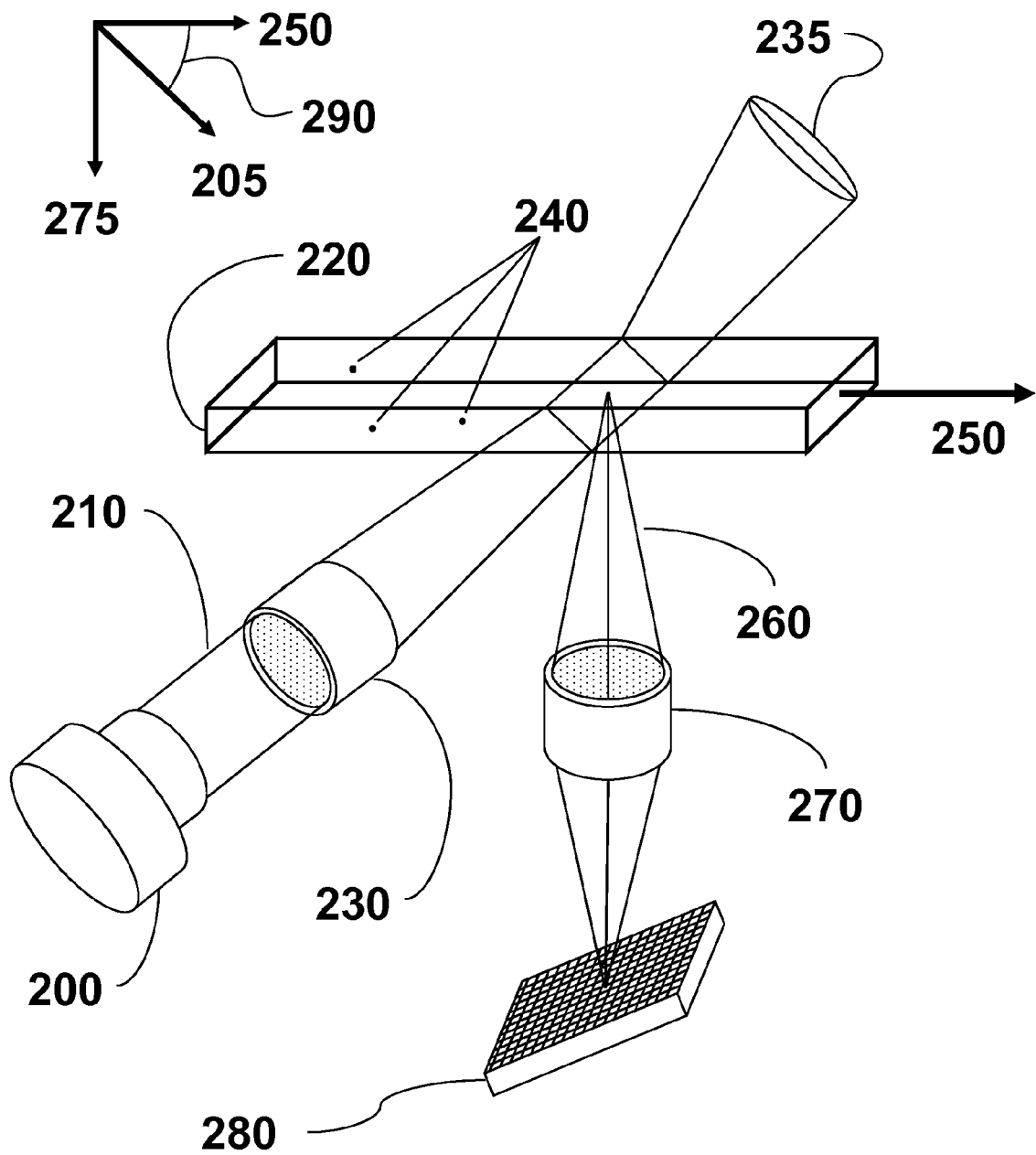
FIG. 2A provides a perspective view of an embodiment of a particle detection system.

FIG. 2A shows a perspective view of a particle detection system embodiment. In this embodiment, source 200 generates a beam of electromagnetic radiation 210 which is directed through flow cell 220. Beam 210 is shaped and directed by a lens 230 before entering flow cell 220. In this embodiment, beam 210 is shaped by lens 230 to have a cross sectional profile 235 having an elliptical shape having a major axis parallel to axis 205 and a propagation axis orthogonal to flow direction 250. Particles 240 flow through flow cell 220 parallel to flow direction 250. Cross sectional profile major axis 205 forms an angle 290 with flow direction 250. Particles flow through the region of the flow cell 220 that is illuminated by beam 210 and interact with the beam, generating scattered or emitted electromagnetic radiation 260. Scattered or emitted electromagnetic radiation 260 is collected and directed by optical system 270 onto two-dimensional detector 280 along optical detection axis 275. In this embodiment, two-dimensional detector 280 is non-orthogonal to optical detection axis 275.

Figure 2B:
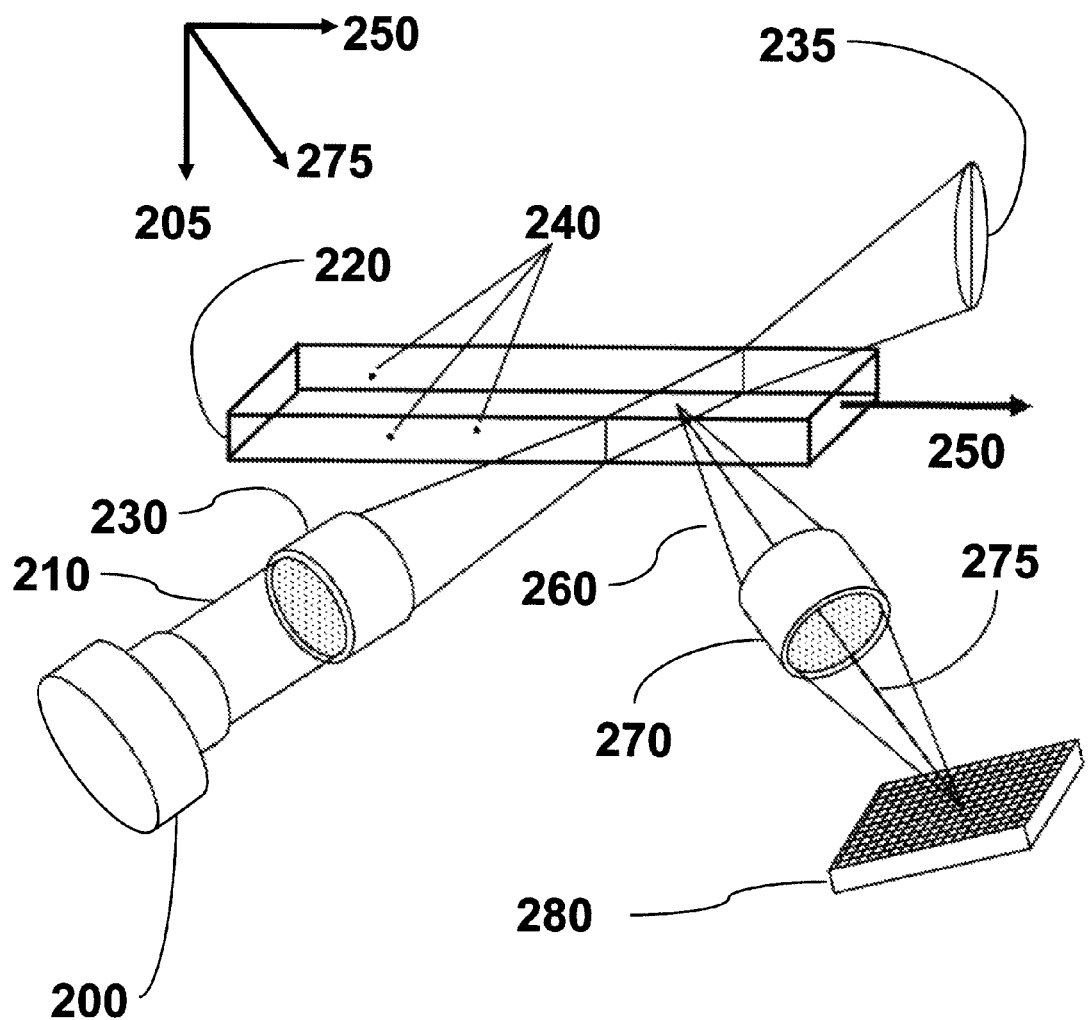
FIG. 2B provides a perspective view of an embodiment of a particle detection system.

FIG. 2B shows a perspective view of an alternative particle detection system embodiment. In this embodiment, source 200 generates a beam of electromagnetic radiation 210 which is directed through flow cell 220. Beam 210 is shaped and directed by a lens 230 before entering flow cell 220. In this embodiment, beam 210 is shaped by lens 230 to have a cross sectional profile 235 having an elliptical shape having a major axis parallel to axis 205 and a propagation axis non-orthogonal to flow direction 250. Particles 240 flow through flow cell 220 parallel to flow direction 250. In this embodiment, flow direction 250 and cross sectional profile major axis 205 are orthogonal. Particles flow through the region of the flow cell 220 that is illuminated by beam 210 and interact with the beam, generating scattered or emitted electromagnetic radiation 260. Scattered or emitted electromagnetic radiation 260 is collected and directed by optical system 270 onto two-dimensional detector 280 along optical detection axis 275. In this embodiment, two-dimensional detector 280 is non-orthogonal to optical detection axis 275.

Figure 3A:
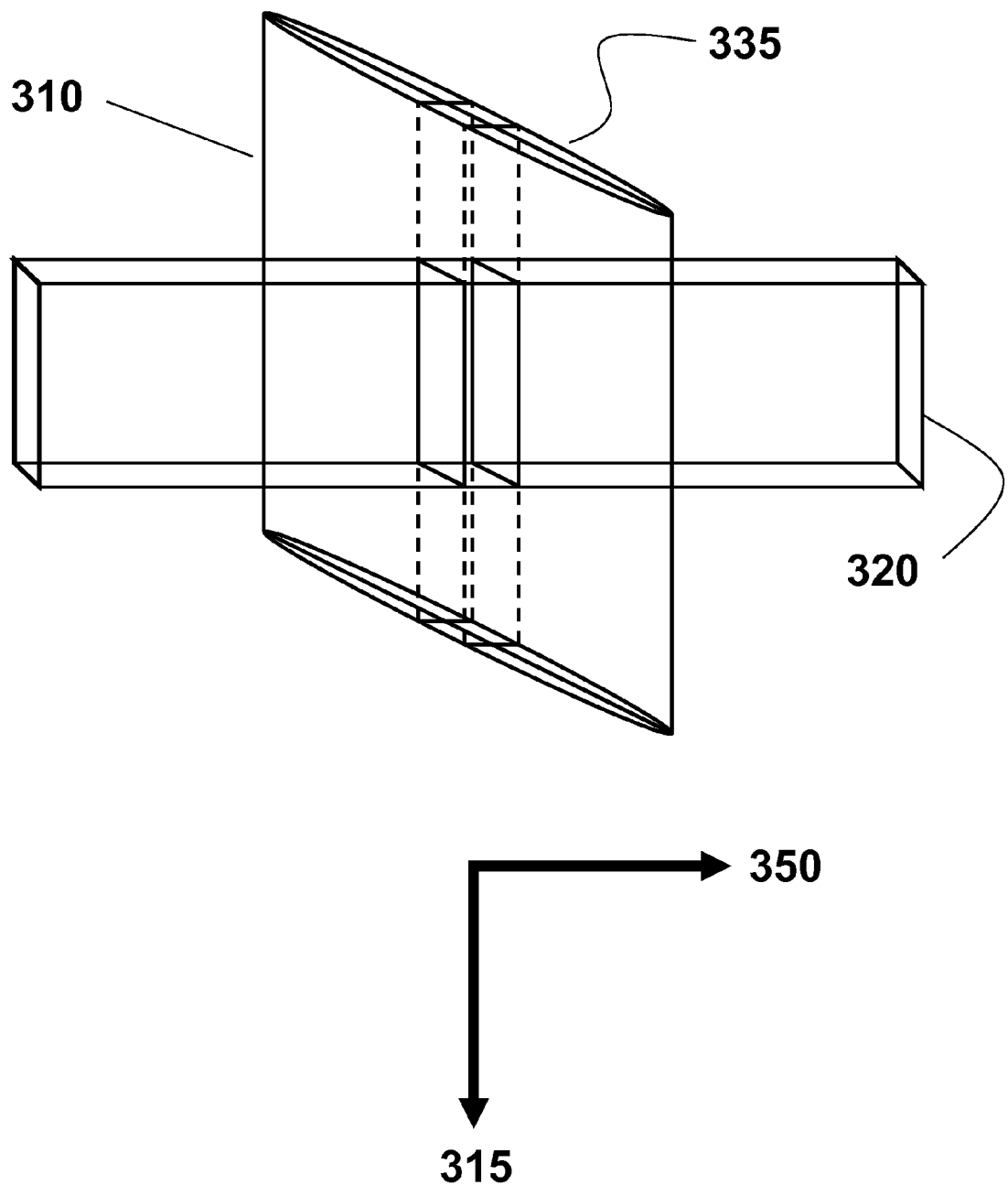
FIG. 3A shows an alternative perspective of a beam of electromagnetic radiation illuminating a flow cell in a particle detection system.
Figure 3B:
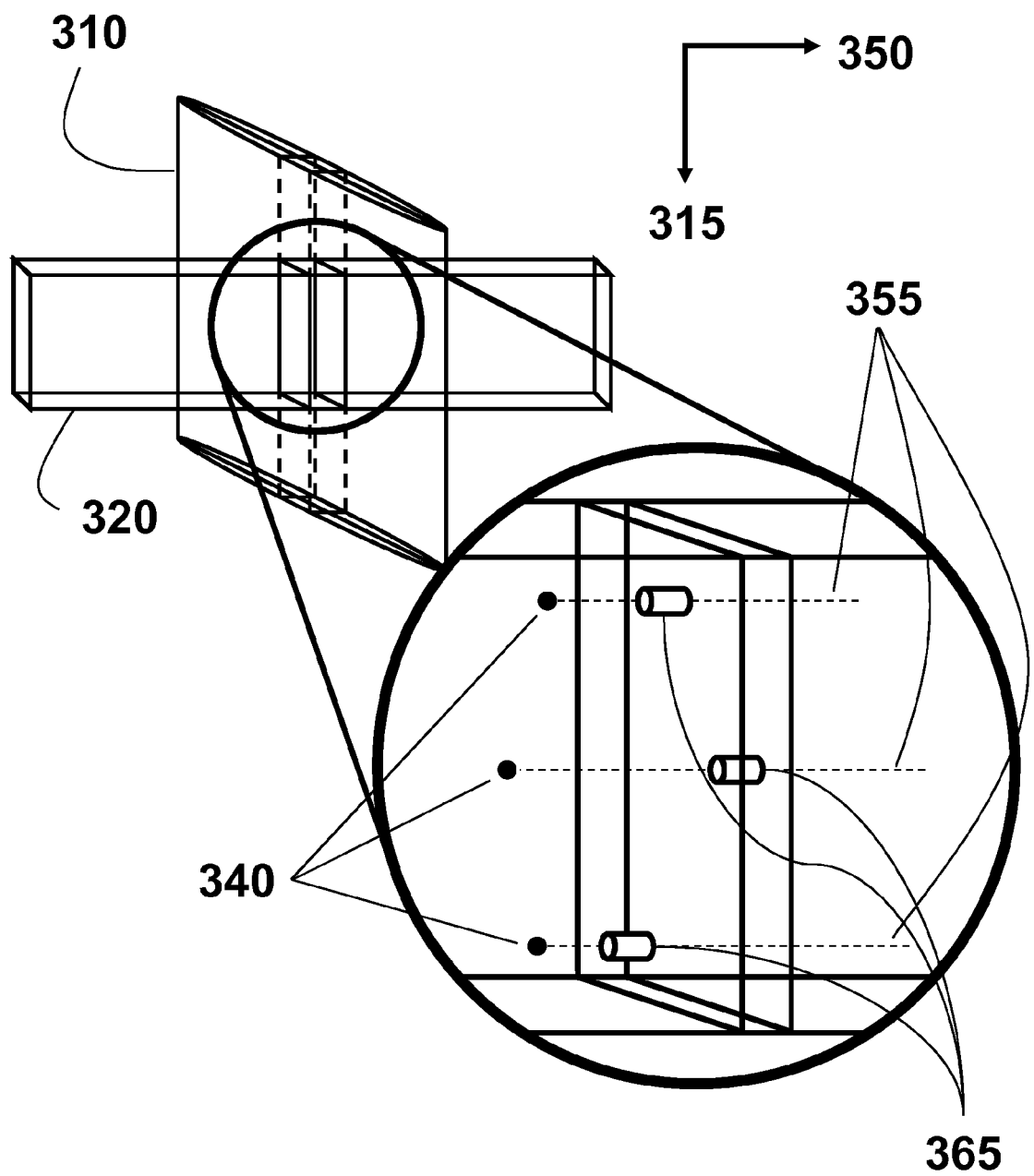
FIG. 3B shows an expanded view of a region of FIG. 3A.
Figure 3C:
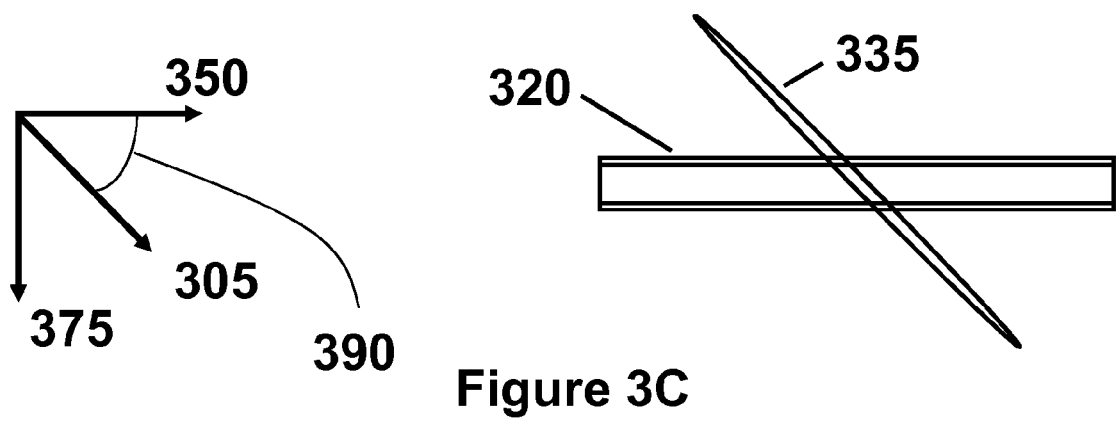
FIG. 3C shows an overhead view of the flow cell of FIG. 3A.
Figure 3D:
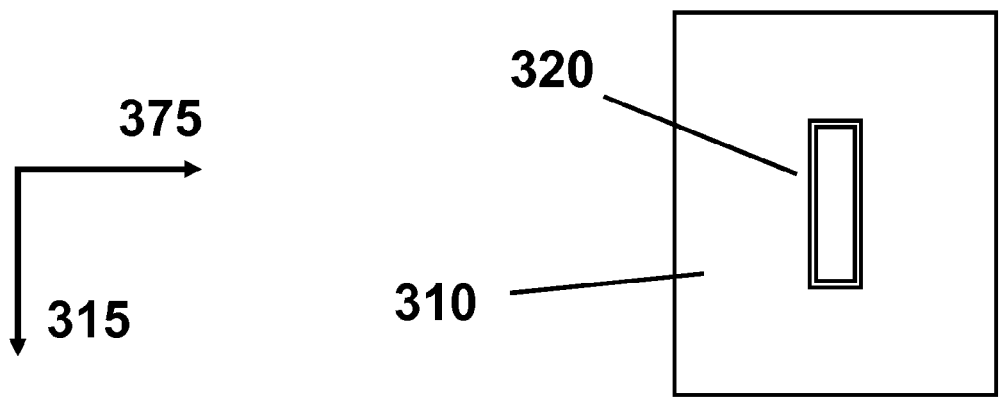
FIG. 3D shows a view of the flow cell of FIG. 3A along the fluid flow direction.
Figure 3E:
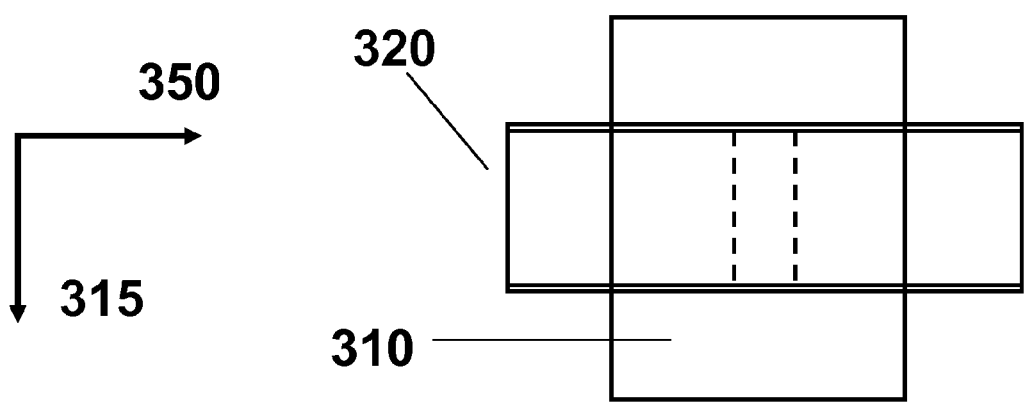
FIG. 3E shows a side view of the flow cell of FIG. 3A.

FIG. 3A shows an alternative perspective view of the beam of electromagnetic radiation illuminating the flow cell. In this figure, beam 310 is traveling parallel to beam propagation axis 315. Particles and fluid flowing in flow cell 320 travel parallel to flow direction 350. FIG. 3B shows an expanded view of a region of flow cell 320. Particles 340 travel parallel to flow direction 350 along trajectories 355 and interact with beam 310 in regions 365 where they generate scattered or emitted electromagnetic radiation. FIGS. 3C, 3D, and 3E show various views of the flow cell 320 and beam 310. FIG. 3C shows a view of the flow cell 320 and beam looking along the propagation axis of the beam. The cross sectional profile 335 of the beam is shown in this view. In this embodiment, cross sectional profile 335 has an elliptical shape. FIG. 3C also shows a set of axes for this view showing flow direction 350, an optical collection axis 375 and beam cross sectional profile major axis 305. Angle 390 is formed between flow direction 350 and beam cross sectional profile major axis 305. In various embodiments, angle 390 is different from 90°; that is, flow direction 350 and beam cross sectional profile major axis 305 are non-orthogonal. In some embodiments, however, angle 390 is 90°. FIG. 3D shows a view of flow cell 320 looking along flow direction. Beam 310 propagates along beam propagation axis 315 illuminating flow cell 320. Scattered or emitted electromagnetic radiation generated by particles interacting with beam 310 is collected along optical collection axis 375. FIG. 3E shows a view along the optical collection axis. Particles and fluid flow in flow direction 350 through flow cell 320. Beam 310 propagates along beam propagation axis 315 illuminating flow cell 320. In this embodiment, only a small portion of flow cell 320 is illuminated by beam 310. The illuminated region is indicated by the dashed lines in FIG. 3E. However, all of the fluid flows through the beam.

The invention may be further understood by the following non-limiting example:

EXAMPLE 1

Particle Detector Images and Counting Efficiencies

Figure 4A:
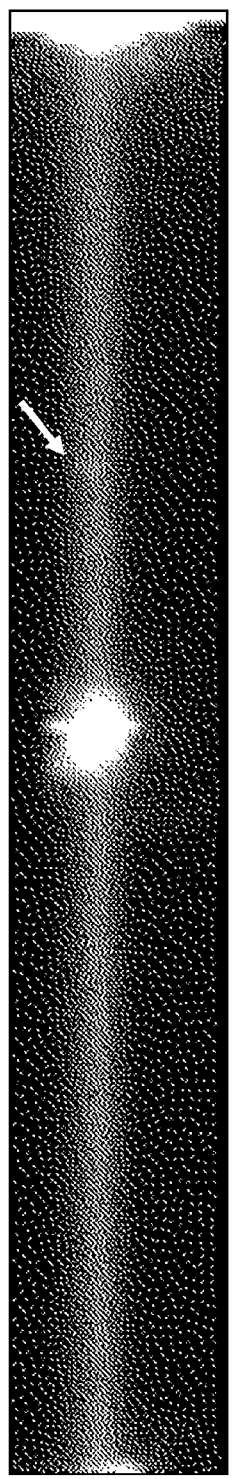
FIG. 4A shows an image detected by a two-dimensional detector of a particle detection system, where the angle between the beam cross sectional profile major axis and the flow direction is 90°.
Figure 4A:
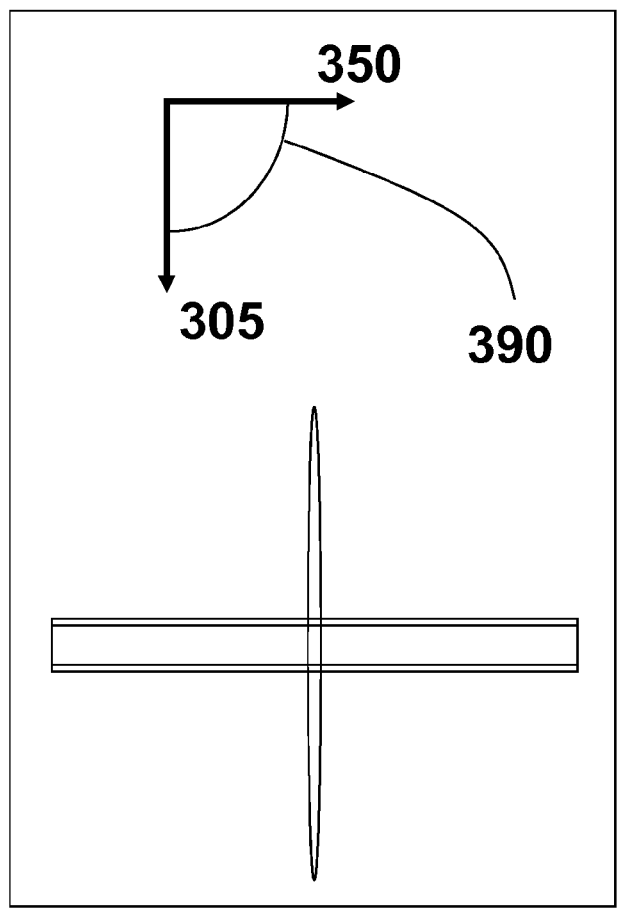
Figure 4A:
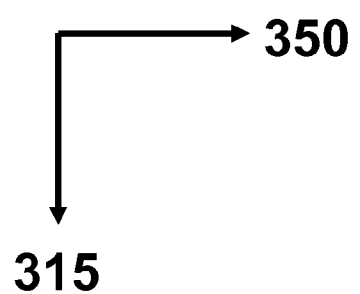
Figure 4B:
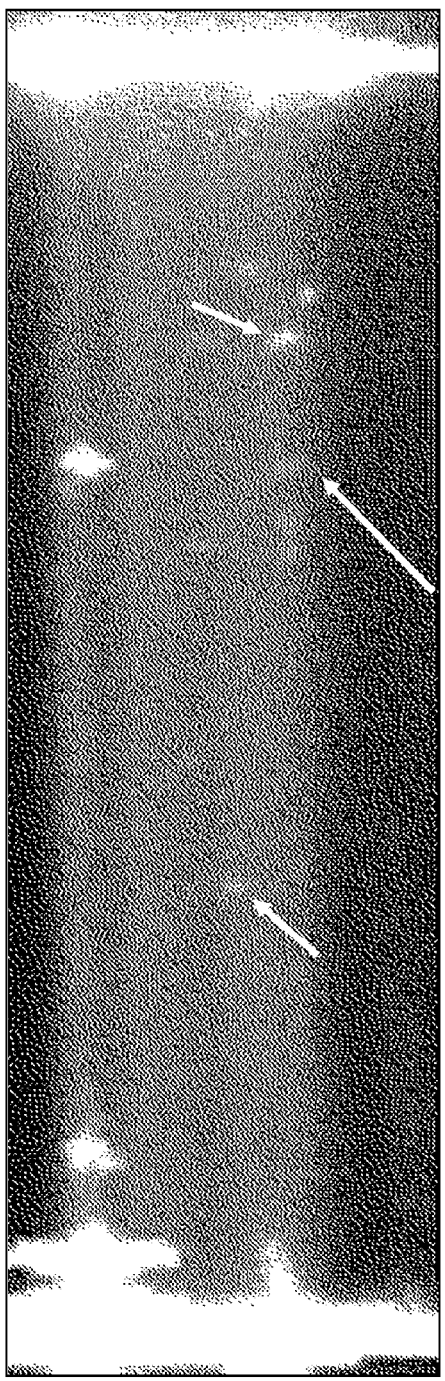
FIG. 4B shows an image detected by a two-dimensional detector of a particle detection system, where the angle between the beam cross sectional profile major axis and the flow direction is 45°.
Figure 4B:
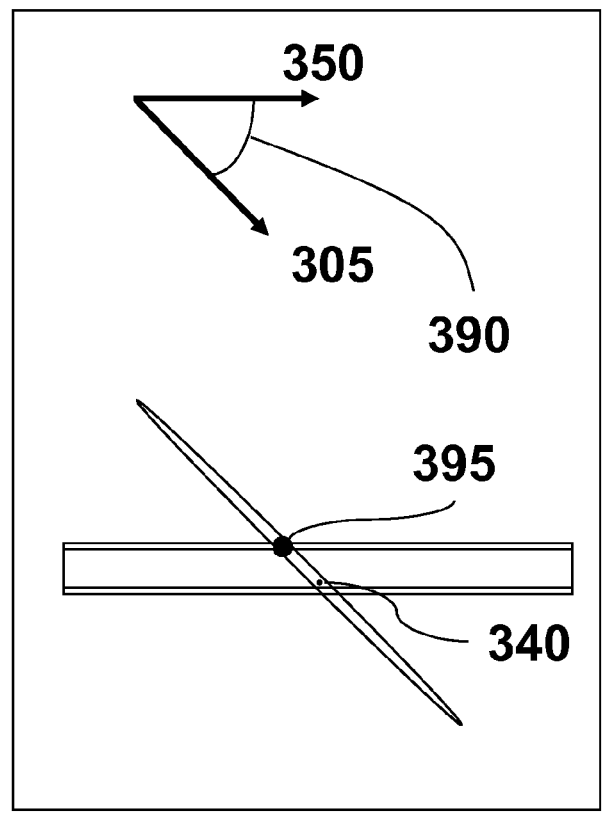
Figure 4B:
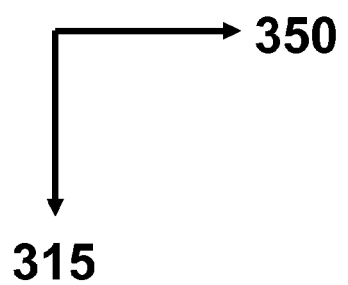
Figure 4C:
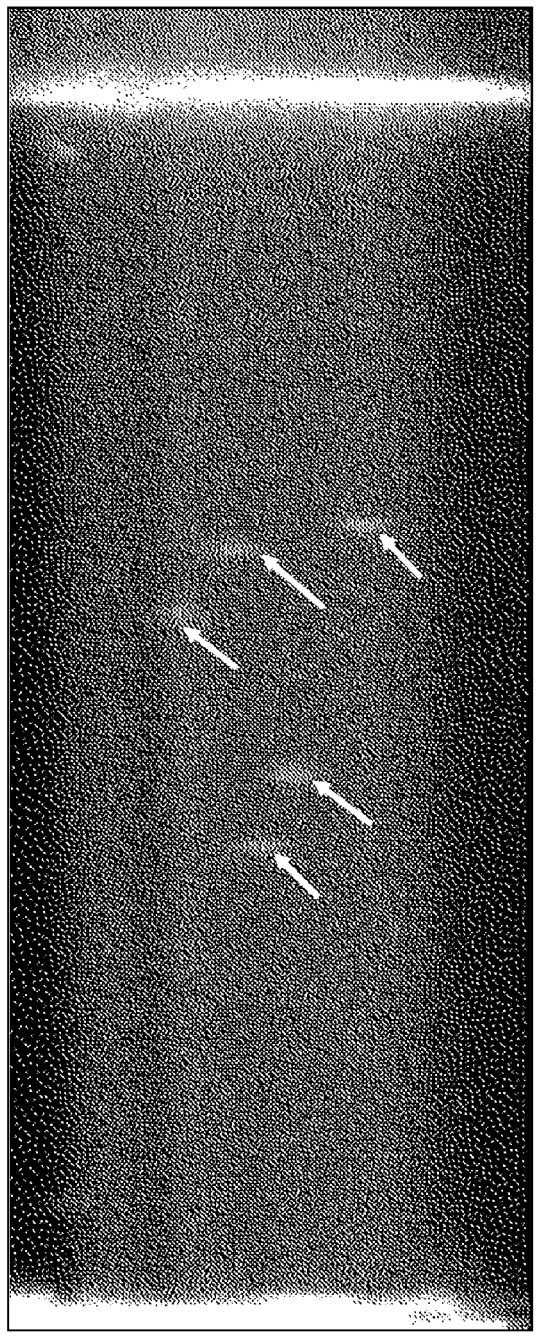
FIG. 4C shows an image detected by a two-dimensional detector of a particle detection system, where the angle between the beam cross sectional profile major axis and the flow direction is 21°.
Figure 4C:
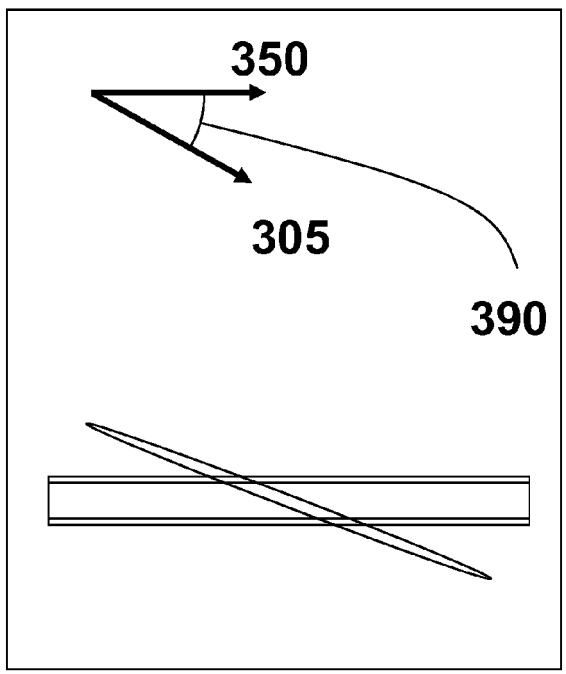
Figure 4C:
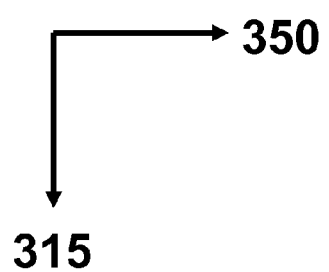

FIGS. 4A, 4B, and 4C show images detected by a two-dimensional detector of a particle detection system embodiment for various angles between the flow direction and beam cross sectional profile major axis. These grey-scale images represent intensities observed by a two-dimensional detector where black is low intensity and white is high intensity. These images represent a view of the flow cell similar to that of FIG. 3E. In these images, the bright white spot at the top of the image represents scattered or emitted electromagnetic radiation generated by the beam interacting with the walls of the flow cell where the beam enters the flow cell. The bright white spot at the bottom of the image represents scattered or emitted electromagnetic radiation generated by the beam interacting with the walls of the flow cell where the beam exits the flow cell. In these images, particles having a size of 125 nm are travelling in the fluid along flow direction 350, and the beam is propagating along axis 315. The insets in these images show views of the flow cell along the beam propagation axis, showing the orientation of the beam cross sectional profile major axis 305 in relation to the flow cell and flow direction 350.

In FIG. 4A, beam cross sectional profile major axis 305 is perpendicular to flow direction 350; i.e., angle 390 is 90°. The bright white spot in the center of the image is a result of contamination on the walls of the flow cell. The faint line travelling from the top of the image to the bottom of the image represents electromagnetic radiation scattered by fluid in the flow cell interacting with beam which propagates along axis 315. In the image in FIG. 4A, a faint spot brighter than its surroundings may indicate detection of a single particle (indicated by an arrow in the image). The bright white spot is likely the result of contamination located on the walls of the flow cell interacting with the beam. In this orientation, electromagnetic radiation scattered or emitted by contamination such as this falls along regions of the flow where particles may travel, thus obscuring detection of particles from these region. When angle 390 is different from 90°, contamination on the walls of the flow cell will be appear towards the left or right side of the image and not obscure such large regions.

In FIG. 4B, beam cross sectional profile major axis 305 and flow direction 350 form an angle 390 of approximately 45°. The two bright white spots along the left side of the image are a result of contamination on the walls of the flow cell. As mentioned before, since the cross-sectional profile of the beam is now at an angle 390 of 45°, the scattered or emitted electromagnetic radiation from the contamination no longer obscures major portions of the flow region, but appears at the sides of the image. The faint glow travelling from the top of the image to the bottom of the image represents electromagnetic radiation scattered by fluid in the flow cell interacting with beam propagating along axis 315. In the image in FIG. 4B, several faint spots brighter than the surroundings may indicate detection of particles (3 examples indicated by arrows in the image). With the geometrical configuration of FIG. 4A, where angle 390 is 90°, the particle indicated by the long arrow would likely be obscured from detection due to the topmost bright contamination spot located on the left side of the image. This shows a useful advantage of the non-orthogonal geometry in reducing noise and increasing detection efficiency and sensitivity. Additionally, when beam cross sectional profile major axis 305 is non-orthogonal to flow direction 350, such as in FIG. 4B, the location that scattered or emitted radiation is detected on the two-dimensional detector is related to the position of the origin of the scattered or emitted radiation in the flow cell. For example, the bright contamination spot on the left side of the image appears to be from contamination on one side of the flow cell, as indicated by element 395 in the inset, while the particle indicated by the long arrow appears to be from a particle travelling near the opposite side of the flow cell, as indicated by element 340 in the inset.

In FIG. 4C, beam cross sectional profile major axis 305 is aligned to flow direction 350 at an angle 390 of approximately 21°. The faint glow travelling from the top of the image to the bottom of the image represents electromagnetic radiation scattered by fluid in the flow cell interacting with beam propagating along axis 315. In the image in FIG. 4C, several faint spots brighter than the surroundings indicate detection of particles (5 examples indicated by arrows in the image). Aside from separating scattered or emitted electromagnetic radiation from the walls of the walls of the flow cell, when beam cross sectional profile major axis 305 is non-orthogonal to flow direction 350, the particles have a longer distance to travel through the beam, resulting in more light scattered and smaller particles able to be detected.

Figure 5:
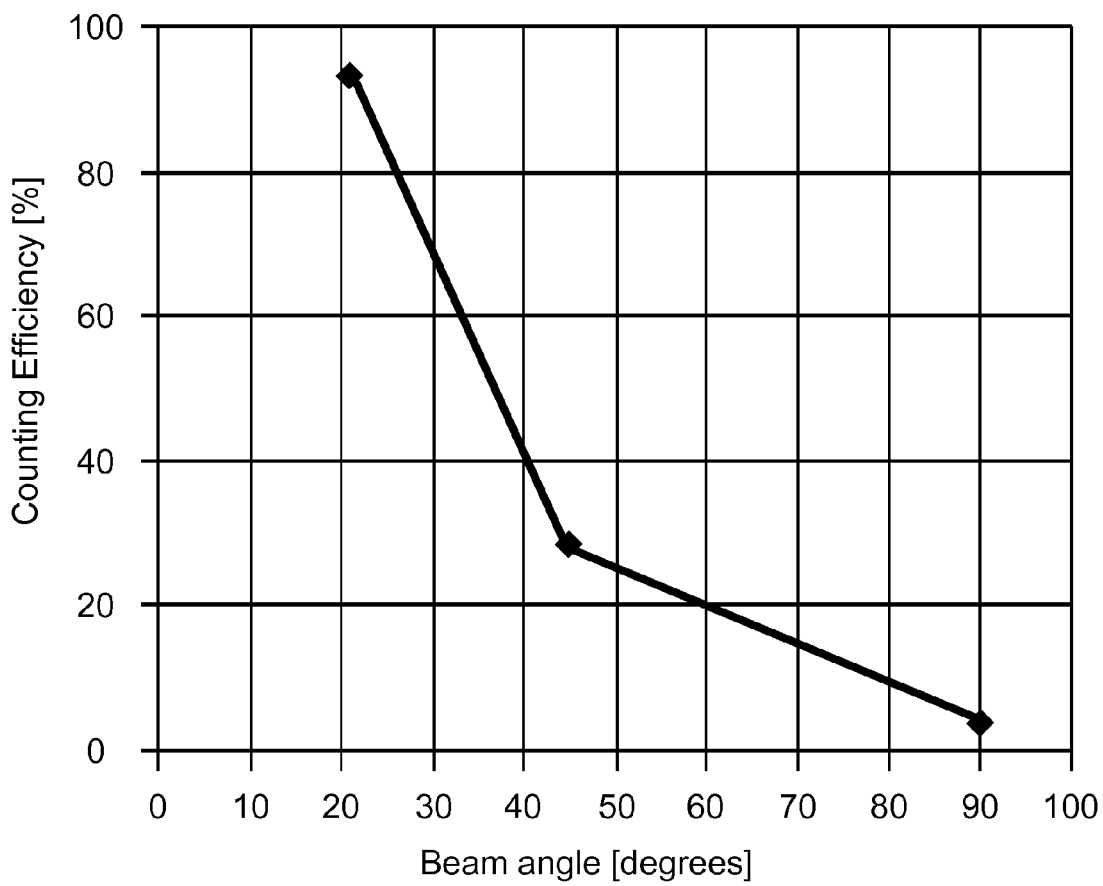
FIG. 5 shows data illustrating the counting efficiency of 80 nm particles by a particle detection system at various angles between the beam cross sectional profile major axis and the flow direction.
Figure 6:
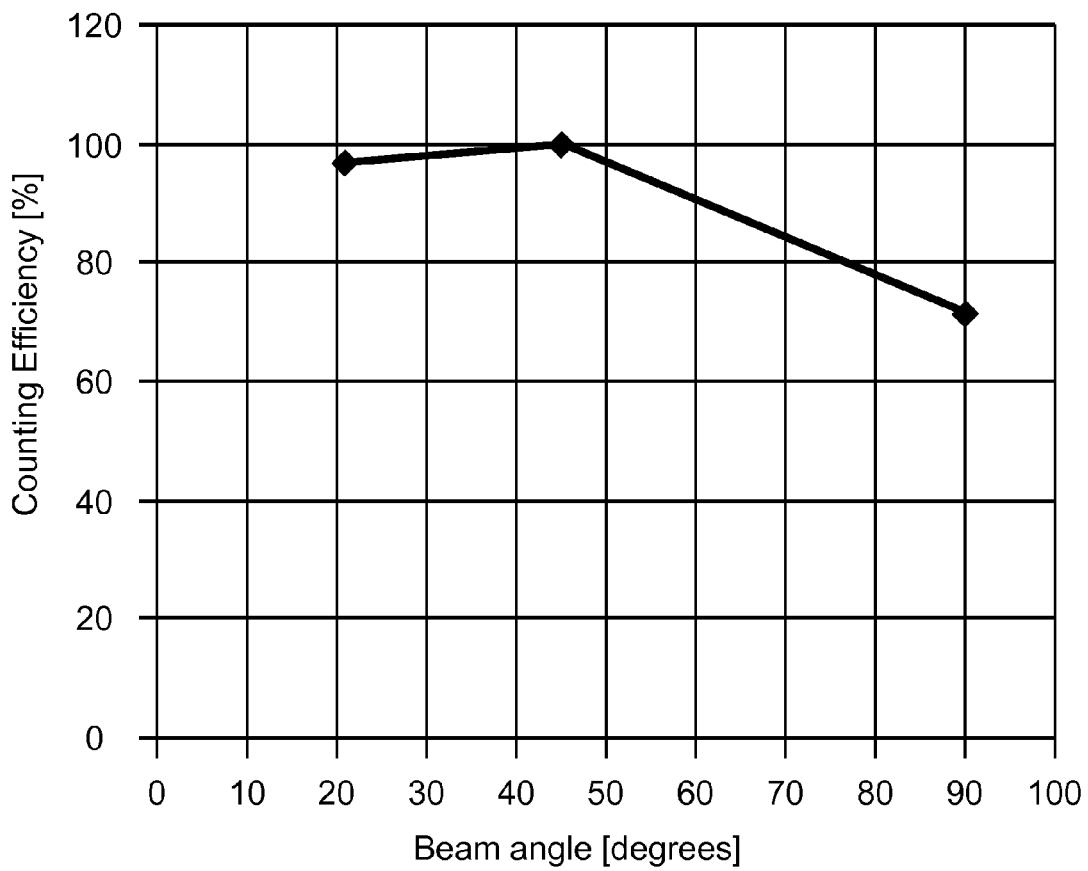
FIG. 6 shows data illustrating the counting efficiency of 125 nm particles by a particle detection system at various angles between the beam cross sectional profile major axis and the flow direction.
Figure 7:
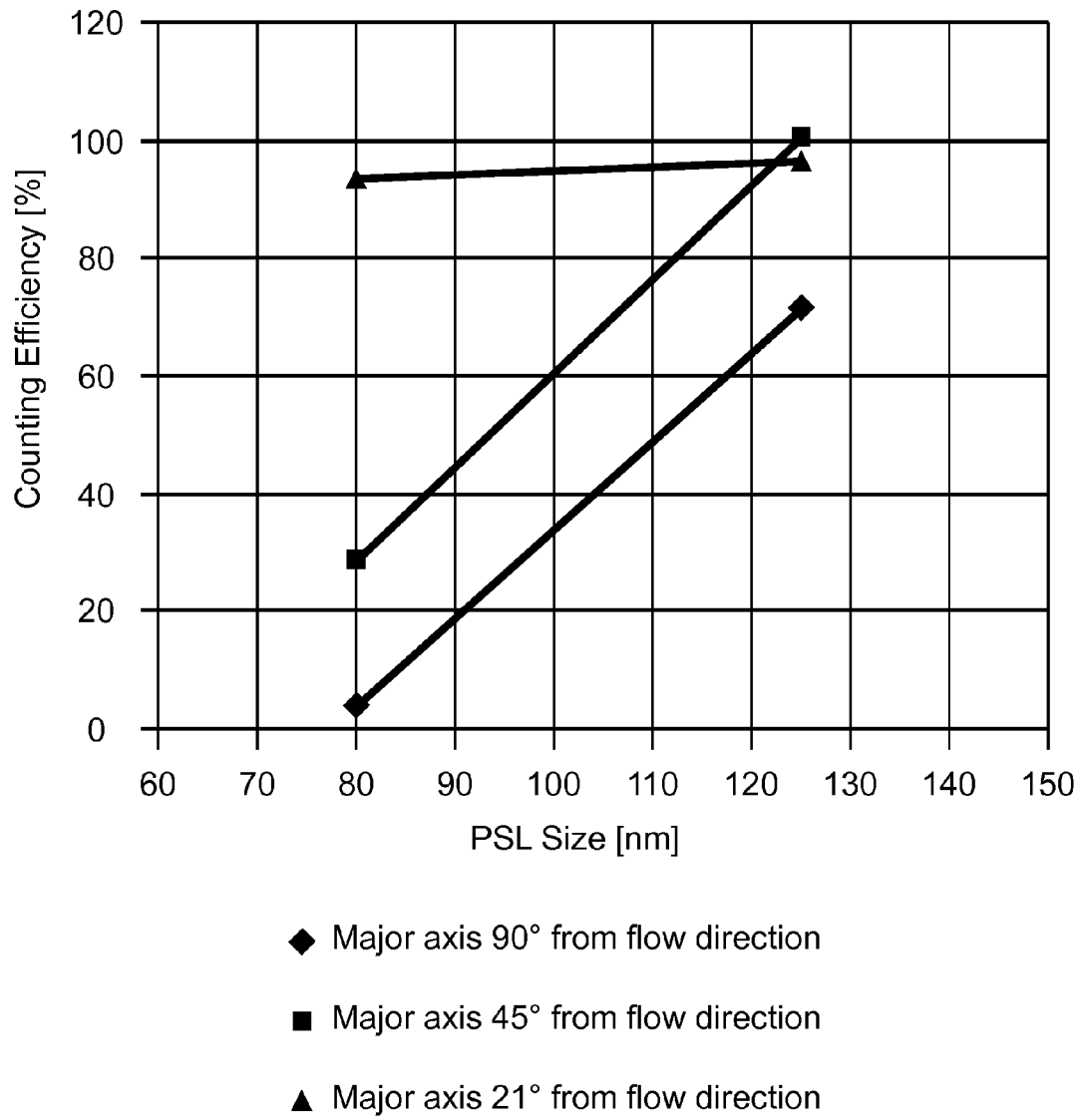
FIG. 7 shows data summarizing the counting efficiency of 80 and 125 nm particles at various angles between the beam cross sectional profile major axis and the flow direction.

Polystyrene latex particles having sizes of 80 nm and 125 nm were allowed to flow through a particle detection system in order to determine the counting efficiency of the particles. The angle between the flow direction and the beam cross sectional profile major axis was varied at 3 directions: a 21° angle between the flow direction and the beam cross sectional profile major axis; a 45° angle between the flow direction and the beam cross sectional profile major axis; and a 90° angle between the flow direction and the beam cross sectional profile major axis. FIG. 5 shows data illustrating the counting efficiency of 80 nm particles as a function of the angle between the flow direction and beam cross sectional profile major axis. As seen in FIG. 5, the counting efficiency of the 80 nm particles drops as the angle is increased from 21° to 45° to 90°. FIG. 6 shows similar data illustrating the counting efficiency of 125 nm particles. As seen in FIG. 6, the counting efficiency of 125 nm particles is near 100% at 21° and 45°, but has a significant drop off to less than 80% counting efficiency at an angle of 90°. FIG. 7 summarizes the counting efficiency of 80 nm and 125 nm polystyrene latex particles.

EXAMPLE 2

Capillary Mount for Particle Counting with Integral Seals

One issue that has plagued liquid particle counters is the lack of a chemically resistant seal for sealing sample capillaries to a flow cell. An approach to solve this problem uses a holder or a mount comprising a nonreactive and virtually rigid polymer, for example Kel-f at 80 Shore D, to create a seal with a capillary inlet. The holder or mount includes one or more concentric seals around a capillary aperture integral to the holder or mount. This cuts the number of potential leak paths, eliminates components that can be incorrectly installed and reduces the number of tolerances to insure a more uniform seal pressure. In embodiments, a particle counter or particle detection system comprises such a capillary mount.

Imaging-based particle counters of the present invention optionally include capillary mounts for particle counting with integral seals, for example, using a rigid polymer (e.g., Kel-f at 80 Shore D) that is formed either by machining or molding to create a series of concentric seals around a capillary aperture integral to the holder. Use of a capillary mount with an integral seal is beneficial for some applications as it cuts the number of potential leak paths, eliminates components that can be incorrectly installed and reduces the number of tolerances to ensure a more uniform seal pressure.

Figure 8:
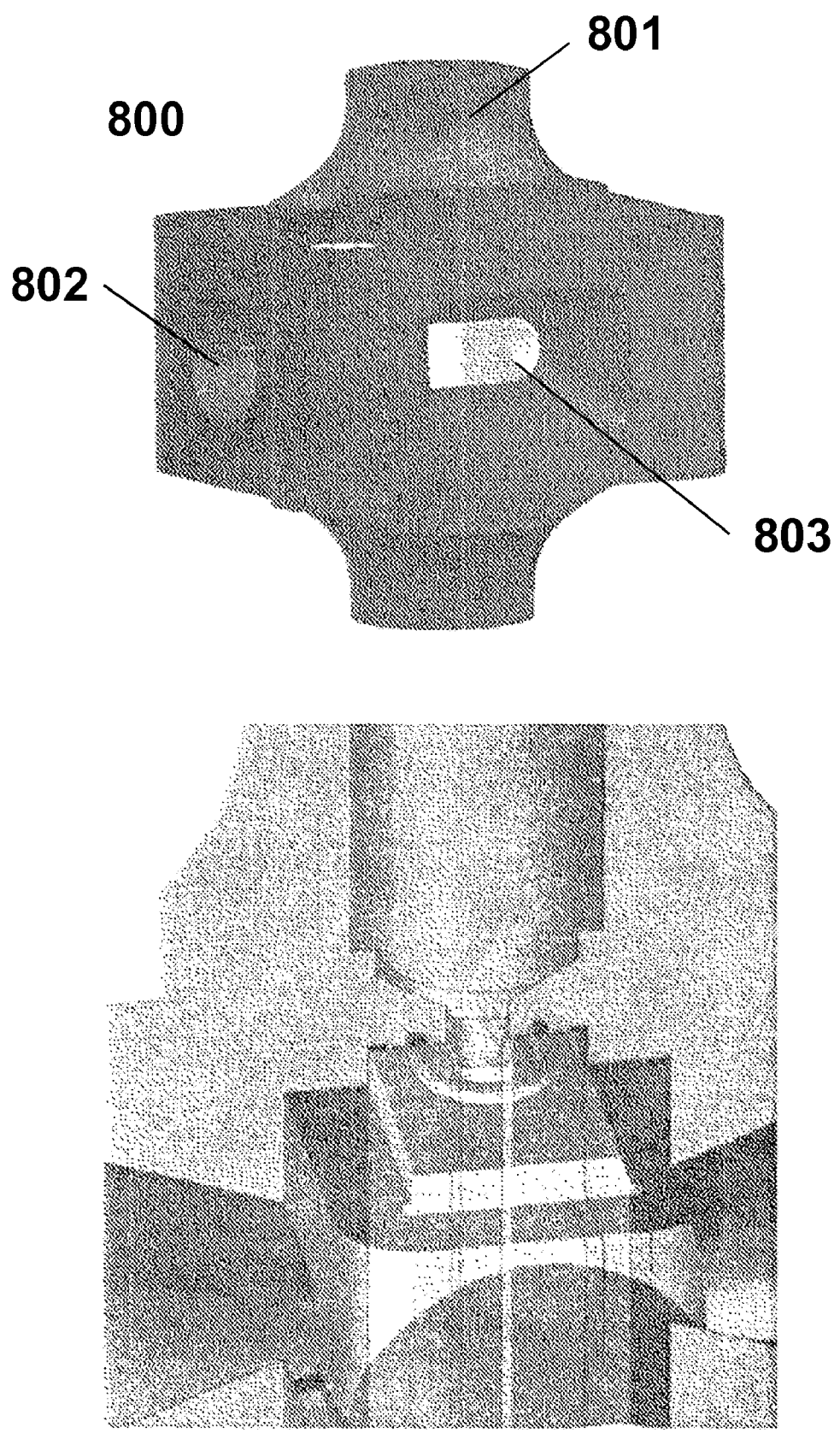
FIG. 8 shows views of an exemplary capillary mount.

FIG. 8 illustrates a perspective view of an exemplary capillary mount 800. Capillary mount 800 includes a plurality of sealing regions 801 for creating a seal with capillary. Capillary mount 800 also includes a flow cell and a plurality of window regions 802 for permitting the entry and exit of a laser beam into the flow cell. Additional window regions 803 are included for transmitting scattered light to a detector. For some embodiments, capillary mount 800 is a unitary structure; that is it comprises a single piece of material for forming a seal with one or more capillaries.

EXAMPLE 3

Autofocus of Non-Orthogonal Particle Detector

In order to maximize particle transit time, coverage area and minimize depth of field, the laser path in a particle detector is tipped relative to a capillary cell. In one embodiment, the beam cross sectional profile major axis is oriented non-orthogonal to the flow direction within the capillary cell. In another embodiment, the beam propagation axis is oriented non-orthogonal to the flow direction within the capillary cell. For example, these axes can be oriented at a relative angle of 69° or 21°. In order to collect the radiation scattered from or emitted by particles in the flow and ensure a proper focus, the detector and capillary are tipped relative to any sensor imaging optics, for example a system of optics as described above. Imaging-based particle counters of the present invention optionally include auto-focusing either particle spot sizes or laser beam structure or a combination of both.

The location of the detector along the optical axis of the imaging optics can be adjusted by translation to achieve the best focus of the scattered or emitted radiation, but must also keep the image in the same location on the detector throughout the range of translation. A method for achieving this comprises mounting the detector at a fixed angle to the optical axis of the imaging optics and translating the detector along the imaging axis to focus. In one embodiment, the detector is mounted on a linear rail system aligned to the optical axis for translating the detector along the optical axis. In a specific embodiment, a spring is mounted to preload the imaging optics against one side of an angled plane to increase the precision of a translation stepper motor (e.g., by a factor of 5 or greater), to allow for a smaller increment of linear motion (e.g., 2 µm or less) per stepper motor step. In an embodiment, a particle counter or particle detection system comprises an autofocus system.

Figure 9:
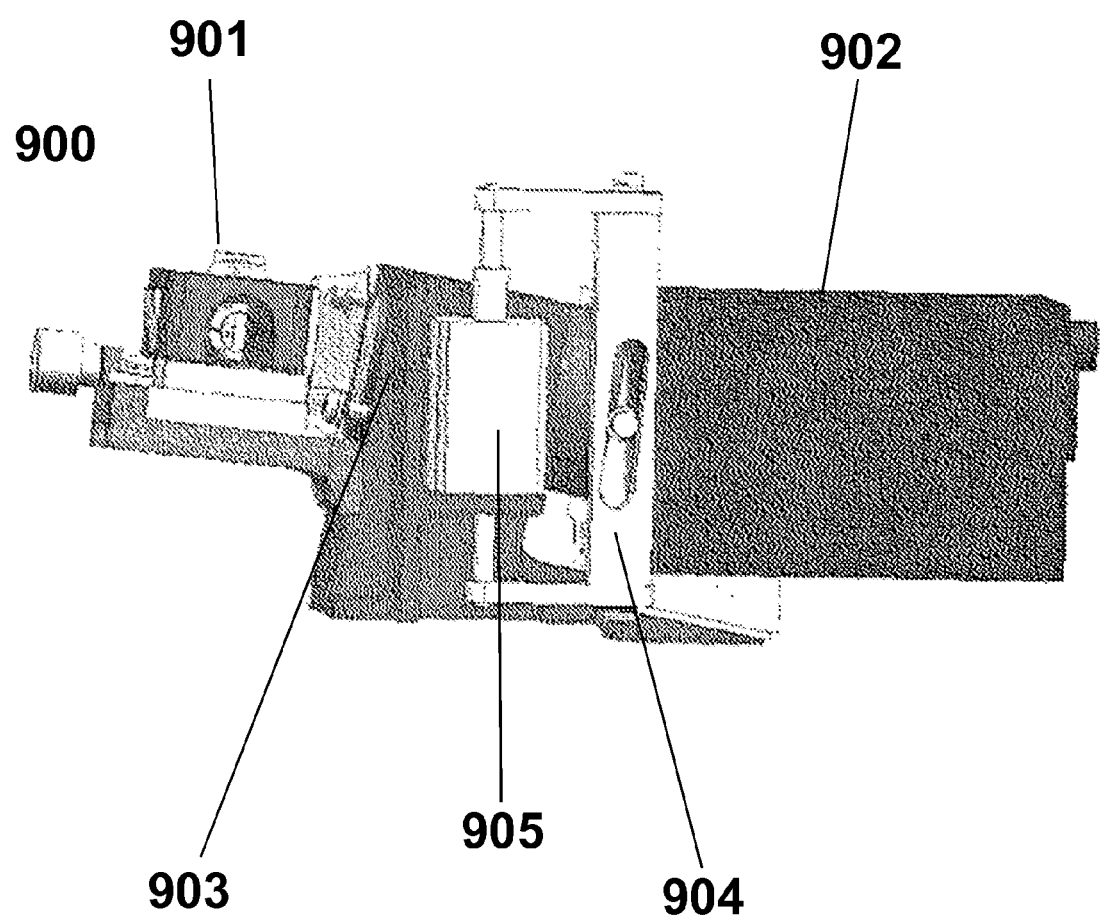
FIG. 9 illustrates an exemplary autofocus system.

FIG. 9 illustrates a specific autofocusing system embodiment 900. A capillary cell is mounted in capillary mount 901 and detector 902 is mounted at an angle relative to imaging optics housed within block 903. A linear rail system 904 is attached to detector 902 and stepper motor 905 for translation of detector 902 along the optical axis of the imaging optics housed within block 903.

EXAMPLE 3

Detector Array Processing

In embodiments, electromagnetic radiation is scattered from or emitted by a particle interacting with a beam of electromagnetic radiation of a particle detection system; scattered or emitted electromagnetic radiation which reaches the two-dimensional detector is detected, thereby generating a plurality of output signals corresponding to intensities of the scattered or emitted electromagnetic radiation. These output signals can be further processed and/or analyzed to determine a characteristic of the particle.

For some embodiments, output signals from every element of the two-dimensional detector are recorded or transmitted to a processor for further analysis. For other embodiments, however, output signals from a sub-array (i.e., only a portion) of the elements of the two dimensional detector are recorded or transmitted to a processor for further analysis. In this way, it is possible to select a subset of the two-dimensional detector for use in detecting or sensing a characteristic of a particle. In a specific embodiment, only a portion of the output signals of the sub-array are utilized in determining a characteristic of a particle. Such a region of interest is useful, for example, for producing better size resolution of detected particles and/or preventing growth of the sample volume undergoing detection.

For example, the entire two-dimensional detector may image the entire flow cell of a particle detection system. A specific sub-array may correspond to output signals of an imaged region of a flow cell, for example the region of the flow cell illuminated by a beam of electromagnetic radiation. As another example, a sub-array may correspond to output signals of an imaged region of a flow cell illuminated by a beam of electromagnetic radiation but excluding the walls of the flow cell. A region of interest, for example, may comprise output signals corresponding to the imaged region of a flow cell illuminated by the center of the beam of electromagnetic radiation and/or where the intensity of the beam of electromagnetic radiation is substantially uniform.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference). U.S. Provisional Applications 61/005,336, 60/992,192 and 61/107,397 filed on Dec. 4, 2007, Dec. 4, 2007 and Oct. 22, 2008, respectively, are herein incorporated by reference in their entireties. U.S. Nonprovisional Application entitled "Two-Dimensional Optical Imaging Methods and Systems for Particle Detection" by inventors Mitchell, Sandberg, Sehler, Williamson and Rice and having attorney docket number 171-07 and filed on Dec. 2, 2008 is herein incorporated by reference in its entirety.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A particle detection system comprising:
   a flow cell for containing a fluid flowing through said flow cell in a flow direction;
   a source for generating a beam of electromagnetic radiation having a cross sectional profile having a major axis and a minor axis, said source positioned to direct said beam through said flow cell, wherein an angle between said major axis and said flow direction is non-orthogonal, wherein particles contained within said fluid interact with said beam, thereby generating scattered or emitted electromagnetic radiation;
   a system of optics for collecting and directing said scattered or emitted electromagnetic radiation onto a two-dimensional detector, wherein said system of optics has an optical axis positioned non-orthogonal to said major axis; and
   said two-dimensional detector positioned in optical communication with said flow cell for receiving at least a portion of said scattered or emitted electromagnetic radiation, wherein said two-dimensional detector is positioned non-orthogonal to said optical axis of said system of optics.

2. The particle detection system of claim 1, wherein said two-dimensional detector comprises an array of detector elements positioned such that a plurality of said detector elements receives said scattered or emitted electromagnetic radiation.

3. The particle detection system of claim 1, wherein said angle is selected from the range of 5° to 85°.

4. The particle detection system of claim 1 wherein said cross sectional profile has a shape that is elliptical or rectangular.

5. The particle detection system of claim 1, wherein said cross sectional profile has a width along said minor axis selected from between 5 µm and 100 µm.

6. The particle detection system of claim 1, wherein said cross sectional profile has a width along said major axis selected from between 50 µm and 1200 µm.

7. The particle detection system of claim 1, wherein said cross sectional profile has a width along said major axis extending to or beyond edges of said flow cell.

8. The particle detection system of claim 1, wherein said flow cell has a cross sectional profile having a first longer side parallel to a propagation axis of said beam and a second shorter side perpendicular to said propagation axis of said beam.

9. The particle detection system of claim 8, wherein said first longer side has a width selected from 0.25 mm to 10 mm.

10. The particle detection system of claim 8, wherein said second shorter side has a width selected from 80 µm to 500 µm.

11. The particle detection system of claim 8, wherein an aspect ratio of said flow cell is greater than or equal to 20.

12. The particle detection system of claim 1, wherein a propagation axis of said beam is orthogonal to said flow direction.

13. The particle detection system of claim 1, wherein a propagation axis of said beam is non-orthogonal to said flow direction.

14. The particle detection system of claim 1, wherein said system of optics images said scattered or emitted radiation onto said two-dimensional detector.

15. The particle detection system of claim 1, wherein said scattered or emitted electromagnetic radiation is focused by said system of optics to a spot on said two-dimensional detector having a size selected from between 5 µm to 80 µm.

16. The particle detection system of claim 1, wherein said two-dimensional detector has an orientation positioned to allow for a sharply focused image of said scattered or emitted electromagnetic radiation across an active area of said two-dimensional detector.

17. The particle detection system of claim 1, wherein said two-dimensional detector has an orientation positioned for providing a spatially resolved image of said scattered or emitted electromagnetic radiation, wherein said scattered or emitted electromagnetic radiation is spatially resolved along a first axis parallel to a propagation axis of said beam and a second axis parallel to said major axis of said cross sectional profile of said beam.

18. The particle detection system of claim 1, wherein said two-dimensional detector performs time delay integration.

19. A method of detecting particles, said method comprising the steps of:
providing particles in a fluid having a flow direction;
passing a beam of electromagnetic radiation having a cross sectional profile having a major axis and a minor axis through said fluid, wherein an angle between said major axis and said flow direction is non-orthogonal, and wherein said particles interact with said beam thereby generating scattered or emitted electromagnetic radiation;
collecting and directing said scattered or emitted electromagnetic radiation onto a two-dimensional detector using a system of optics wherein said system of optics has an optical axis positioned non-orthogonal to said major axis; and
detecting at least a portion of said scattered or emitted electromagnetic radiation using said two-dimensional detector, wherein said two-dimensional detector is positioned non-orthogonal to said optical axis of said system of optics, thereby detecting said particles.

20. A method of spatially resolving an interaction of particles with a beam of electromagnetic radiation, said method comprising the steps of:
providing particles suspended within a fluid flowing in a flow direction;
passing a beam of electromagnetic radiation through said fluid, wherein said beam has a cross sectional profile having a major axis and a minor axis and wherein an angle between said major axis and said flow direction is non-orthogonal, and wherein said particles interact with said beam thereby generating scattered or emitted electromagnetic radiation;
collecting and directing said scattered or emitted electromagnetic radiation onto a two-dimensional detector using a system of optics, wherein said system of optics has an optical axis positioned non-orthogonal to said major axis, wherein said two-dimensional detector is positioned non-orthogonal to said optical axis of said system of optics,
detecting at least a portion of said scattered or emitted electromagnetic radiation using said two-dimensional detector, thereby spatially resolving said scattered or emitted electromagnetic radiation in a first direction parallel to a propagation axis of said beam and in a second direction parallel to said major axis of said cross sectional profile of said beam.

21. A method of sizing a particle, the method comprising the steps of:
providing a particle suspended within a fluid flowing in a flow direction through a flow cell;
passing a beam of electromagnetic radiation through said fluid, wherein said beam has a cross sectional profile having a major axis and a minor axis and wherein an angle between said major axis and said flow direction is non-orthogonal, and wherein said particle interacts with said beam thereby generating scattered or emitted electromagnetic radiation;
collecting and directing said scattered or emitted electromagnetic radiation onto a two-dimensional detector using a system of optics, wherein said system of optics has an optical axis positioned non-orthogonal to said major axis, wherein said two-dimensional detector is positioned non-orthogonal to said optical axis of said system of optics,
imaging at least a portion of said scattered or emitted electromagnetic radiation onto the two-dimensional detector;
determining an intensity of said scattered or emitted electromagnetic radiation imaged onto said two-dimensional detector; and
comparing said intensity of said scattered or emitted electromagnetic radiation imaged onto said two-dimensional detector with one or more threshold reference values, thereby determining a size of said particle.

* * * * *